(12) United States Patent
Su et al.

(10) Patent No.: US 8,410,130 B2
(45) Date of Patent: Apr. 2, 2013

(54) SYNTHESIS OF 8H-3A-AZA-CYCLOPENTA[A]INDENES AND 5,10-DIHYDROPYRROLO[1,2-B]ISOQUINOLINES DERIVATIVES AND THEIR USE AS ANTITUMOR THERAPEUTIC AGENTS

(75) Inventors: Tsann-Long Su, Xizhi (TW); Ting-Chao Chou, Paramus, NJ (US)

(73) Assignee: Academia Sinica, Taipei (TW)

( * ) Notice: Subject to any disclaimer, the term of this patent is extended or adjusted under 35 U.S.C. 154(b) by 985 days.

(21) Appl. No.: 12/267,227

(22) Filed: Nov. 7, 2008

(65) Prior Publication Data

US 2009/0117125 A1 May 7, 2009

Related U.S. Application Data

(60) Provisional application No. 60/996,241, filed on Nov. 7, 2007.

(51) Int. Cl.
| | |
|---|---|
| *A61K 31/437* | (2006.01) |
| *A61K 31/403* | (2006.01) |
| *C07D 487/00* | (2006.01) |
| *C07D 221/06* | (2006.01) |

(52) U.S. Cl. ............ 514/290; 514/411; 548/428; 546/79
(58) Field of Classification Search .................... 546/79; 548/428; 514/290, 411
See application file for complete search history.

(56) References Cited

PUBLICATIONS

Dorwald F. A. Side Reactions in Organic Synthesis, 2005, Wiley: VCH, Weinheim p. IX of Preface.*
Anderson, W. K and Howard L. McPherson. Vinylogous carbinolamine tumor inhibitors. 11. Synthesis and antileukemic activity of fluorinated analogs of 2,3-dihydro-5-phenyl-6,7-bis(hydroxymethyl)-1H-pyrrolizine biscarbamate. J. Med. Chem. 1982, 25, 84-86.
Anderson, W. K and Michael J. Halat. Vinylogous carbinolamine tumor inhibitors. Antileukemic activity of derivatives of 1,2-dimethyl-3,4-bis(hydroxymethyl)-5-phenylpyrrole bis(N-methylcarbamate). J. Med. Chem. 1979, 22, 977-980.
Anderson, W. K, Chiung Pin Chang, and Howard L. McPherson. Synthesis, evaluation of chemical reactivity, and murine antineoplastic activity of 2-hydroxy-5-(3,4-dichlorophenyl)-6,7-bis(hydroxymethyl)-2,3-dihydro-1H-pyrrolizine bis(2-propylcarbamate) and 2-acyloxy derivatives as potential water-soluble prodrugs. J. Med. Chem. 1983, 26, 1333-1338.
Anderson, W. K, Howard L. McPherson, James S. New, and Arvela C. Rick. Synthesis and murine antineoplastic activity of bis[carbamoyloxymethyl] derivatives of pyrrolo[2,1-a]isoquinoline. J. Med. Chem. 1984, 27, 1321-1325.
Anderson, W. K.; Bhattacharjee, D.; Houstion, D. M. Design, synthesis, antineoplastic activity, and chemical properties of bis(carbamate) derivatives of 4,5-bis(hydroxymethyl)imidazole. J. Med. Chem. 1989, 32, 119-127.
Anderson, W. K.; Corey, P. F. Synthesis and antileukemic activity of 5-substituted 2,3-dihydro-6,7-bis(hydroxymethyl)-1H-pyrrolizine diesters. J. Med. Chem. 1977, 20, 812-818.
Anderson, W. K.; New, J. S.; Corey, P. F. Tumor inhibitory agents. Bis(N-alkylcarbamate) derivatives of 2,3-dihydro-5-(3',4'-dichlorophenyl)-6,7-bis(hydroxymethyl)-1H-pyrrolizine. Arzneim. Forsch. 1980, 30, 765-768.
Carter, S. K.; Crooke, S. T. Mitomycin C: Current Status and New Developments; Academic Press: New York, 1979.
Chou, T.-C. Theoretical basis, experimental design and computerized simulation of synergism and antagonism in drug combination studies. *Pharmacol. Rev.* 2006, 58, 621-681.
Chou, T.-C.; O'Connor, O. A.; Tong, W. P.; Guan, Y.-B.; Zhang, Z.-G.; Stachel, S. J.; Lee, C.; Danishefsky, S. J. The Synthesis, Discovery and Development of a Highly Promising Class of Microtubule Stabilization Agents: Curative Effects of Desoxyepothilones B and F against Human Tumor Xenografts in Nude Mice. *Proc. Natl. Acad. Sci. USA* 2001, 98, 8113-8118.
Chou, T.-C.; Talalay, P. Quantitative Analysis of Dose-Effect Relationships: the Combined Effects of Multiple Drugs or Enzyme Inhibitors. *Adv. Enzyme Regul.* 1984, 22, 27-55.
Doll, C. D., Weiss, R. B., and Issell, B. F. Mitomycin. Ten years after approval for marketing. J. Clin. Oncol. 1985, 3, 276-286.
Elliot, W. L.; Fry, D. W.; Anderson, W. K.; Nelson, J. M.; Hook, K. E.; Hawkins, P. A.; Leopold, W. R. In vivo and in vitro evaluation of the alkylating agent carmethizole. Cancer Res. 1991, 51, 4581-4587.
Grunewald, G. L.; Romero, F. A.; Criscione, K. R. 3-Hydroxymethyl-7-(*N*-substituted aminosulfonyl)-1,2,3,4-tetrahydroisoquinoline Inhibitors of Phenylethanolamine *N*-Methyltransferase that Display Remarkable Potency and Selectivity *J. Med. Chem.*, 2005, 48, 134-140.
Hansson, J,; Lewensohn, R.; Ringborg, U.; Nilsson, B. Formation and removal of DNA cross-links induced by melphalan and nitrogen mustard in relation to drug-induced cytotoxicity in human melanoma cells. *Cancer Res.* 1987, 47, 2631-2637.
Julian, P. L.; Karpel, W. J. Magnani, A.; Meyer, E. W. Studies in indole series. X. Yohimbine (Part 2) The synthesis of yobyrine, yobyrone and "tetrahydroyobyrine". J. Chem. Soc. 1948, 70, 180-183.
Kaprkov, J.; Novkov, O.; Vrna, O.; Farrell, N.; Brabec, V.; Effect of Geometric Isomerism in Dinuclear Platinum Antitumor Complexes on DNA Interstrand Cross-Linking. *Biochemistry* 1999, 38, 10997-10005.
Kloster, M.; Kostrhunova, H.; Zaludova, R.; Malina, J.; Kasparkova, J.; Brabec, V.; Farrell, N.; Trifunctional Dinuclear Platinum Complexes as DNA-Protein Cross-Linking Agents. *Biochemistry*, 2004, 43, 7776-7786.
Oostveen, E. A.; Speckmap, W. N. Mitomycin analogs I. Indoloquinones as potential bis alylating agents. Tetrahedron 1987, 43, 255-262.
Palmer, Brian, D.; Wilson, William, R.; Pullen, Susan, M.; Denny, William, A.; Hypoxia-Selective Antitumor Agents. 3. Relationships between Structure and Cytotoxicity against Cultured Tumor Cells for Substituted N,N-Bis(2-chloroethyl)aniline *J. Med. Chem.* 1990, 33, 112-121.
Satorelli, A. C. Therapeutic attack of solid tumors. Cancer Res. 1988, 48, 775-778.
Scudiero, D. A.; Shoemaker, R. H.; Paull, K. D.; Monks, A.; Tierney, S.; Nofziger, T. H.; Currens, M. J.; Seniff, D.; Boyd, M. R. Evaluation of Soluble Tetrazolium/Formazan Assay for Cell Growth and Drug Sensitivity in Culture Using Human and Other Tumor Cell Lines. *Cancer Res.* 1988, 48, 4827-4833.

(Continued)

*Primary Examiner* — Rita Desai
(74) *Attorney, Agent, or Firm* — Finnegan, Henderson, Farabow, Garrett & Dunner, LLP

(57) ABSTRACT

The present disclosure relates to a series of bis(hydroxymethyl) and its bis(carbamate) of 8H-3a-azacyclopenta[a]indene-1-yl and 5,10-dihydropyrrolo-[1,2-b]isoquinolines derivatives (Formula I-Formula IV) as DNA di-alkylating agents. The preliminary antitumor studies indicated that compounds disclosed herein could exhibit potent cytotoxicity in vitro and antitumor therapeutic efficacy in human tumor xenografts and could have little or no cross-resistance to either Taxol or Vinblastine. The results demonstrated that compounds disclosed herein possess potent antitumor therapeutic efficacy and are expected to have potential for clinical applications.

21 Claims, 7 Drawing Sheets

PUBLICATIONS

Skehan, P.; Storeng, R. H.; Scudiero, D.; Monks, A.; McMahon, J.; Vistica, D.; Warren, J. T.; Bokesch, H.; Kenny, S.; Boyd, M. R. New Colorimetric Cytotoxicity Assay for Anticancer-Drug Screening. *J. Natl. Cancer Inst.* 1990, 82, 1107-1112.

Tomasz, M., and Palom, Y. The mitomycin bioreductive antitumor agents: cross-linking and alkylation of DNA as the molecular basis of their activity. Pharmacol. Ther., 1997, 76, 73-87.

Woo, J.; Sigurdsson, S. T.; Hopkins, P. B. DNA interstrand cross-linking reactions of pyrrole-derived, bifunctional electrophiles: evidence for a common target site in DNA. J. Am. Chem. Soc. 1993, 115, 3407-3415.

\* cited by examiner

SYNTHESIS OF 8H-3A-AZA-CYCLOPENTA [A]INDENES AND 5,10-DIHYDROPYRROLO[1,2-B]ISOQUINOLINES DERIVATIVES AND THEIR USE AS ANTITUMOR THERAPEUTIC AGENTS

This application claims priority under 35 U.S.C. §119(e) to the U.S. provisional patent application No. 60/996,241, filed Nov. 7, 2007, the entire contents of which are incorporated herein by reference.

FIELD OF THE INVENTION

This invention relates to newly synthesized compounds and methods for treating cancer related diseases.

BACKGROUND OF THE INVENTION

Cancer is a group of diseases characterized by uncontrolled growth and spread of abnormal cells. It is anticipated that more than a million new cancer cases will be diagnosed in 2008 in the United States alone. Additionally, more than a half a million Americans are expected to die of cancer during the year 2008, and cancer is exceeded only by heart disease as the most common cause of death in the United States. Cancer Facts & Figures 2008, The American Cancer Society (2008). Therefore, there is a need for additional treatment compounds, strategies, and regimens to address this significant medical problem in the United States and around the world.

Many cancer patients also suffer from drug resistance. In other words, the chemotherapeutic drugs that they have been taking for treatment of their cancer cease to work when the cancer becomes resistant to the drug. Often times, resistance to one drug also generates resistance to other drugs because of commonalities in the mechanisms of action between drugs. This, of course, increases the problems faced by the patient as not only is the drug they were taking ineffective, but other drugs are now ineffective as well. This is termed multidrug resistance. Thus, while many cancer treatments exist currently, there is always a need for more treatment options, especially those that do not have cross resistance when a patient becomes resistant to another initial treatment.

Multiple cancer chemotherapy agents exist in the prior art; however, for the reasons identified, they are insufficient. A large number of synthetic compounds or naturally occurring products contain two reactive nucleophilic centers in the molecule. These compounds often exhibit potent antitumor activity since they can covalently bind to DNA. The synthetic N-mustards (Palmer B D et al., *J. Med. Chem.* 1990, 33, 112-121), which contain N,N-bis(2-chloroethyl)amine active pharmacophore and cis-platinum complexes (Kasparkova J. et al., *Biochemistry* 1999, 38, 10997-10005; Kloster M et al., *Biochemistry*, 2004, 43, 7776-7786) have been the most widely used DNA-interstrand cross-linking agents. Due to their abilities to damage DNA molecules, many antitumor N-mustards are currently used clinically for cancer chemotherapy (Hansson J. *Cancer Res.* 1987, 47, 2631-2637). For instance, the antibiotic anticancer mitomycin C (MMC, 1, FIG. 1) (Tomasz M et al., *Pharmacol. Ther.*, 1997, 76, 73-87; Doll C D et al., *J. Clin. Oncol.* 1984, 3, 276-286; Satorelli A C, *Cancer Res.* 1988, 48, 775-778) and its analogue, indoloquinone EO9 (2), (Oostveen E A et al., *Tetrahedron* 1987, 43, 255-262), which are bifunctional alkylating agents that are able to cross-link to DNA double strands after bioreductive activation (Carter S K et al., Mitomycin C: Current Status and New Developments; Academic Press: New York, 1979). Another class of dialkylating agents, bis(hydroxymethyl)pyrrolizidines and the corresponding bis(carbamates), have certain similarities with mitomycins. The "vinylogoues carbinolamines," such as thioimidazoles (carmethizole, 3)(Anderson W K et al., *J. Med. Chem.* 1989, 32, 119-127; Elliot W L et al., *Cancer Res.* 1991, 51, 4581-4587) 2,3-dihydroxy-6,7-bis(hydroxymethyl)-1H-pyrrolizine[4 (IPP), 5, and 6, FIG. 1] (Anderson W K et al., *Arzneim. Forsch.* 1980, 30, 765-768; Anderson W K et al., *J. Med. Chem.* 1977, 20, 812-818) and bis-alcohols 7, were developed initially from the pyrrolizine alkaloids as DNA alkylators. Among these agents, the bis (carbamates) derivatives exhibited significant antitumor activity and afforded "cures" at low dose in the in vivo P-388 assay (Anderson W K et al., *J. Med. Chem.* 1977, 20, 812-818). These derivatives are capable of forming an interstrand cross-link with the short oligonucleotide 5'-ACGT at the 5'-CG residues at the minor groove region (Woo J et al., *J. Am. Chem. Soc.* 1993, 115, 3407-3415).

The mechanism of action of bis(carbamate)pyrroles or pyrrolizines was proposed to be able to cross-link with DNA doubled strands via $S_N 1$ electrophilic reaction (Anderson W K et al., *J. Med. Chem.* 1977, 20, 812-818; Woo J et al., *J. Am. Chem. Soc.* 1993, 115, 3407-3415). It is speculated that the potential electrophilic reactivity in these agents (via O-alkyl cleavage) can be enhanced by participating the lone pair electron on the ring nitrogen similar to that of MMC derivatives. In other words, it might be possible to affect the cytotoxicity of these congeners by inducing the electronic effects through the substituted phenyl groups at C2 of pyrroles or C5 of pyrrolizines. However, it was reported that the in vivo antileukemic activity and the host toxicity were not altered to a considerable degree as a function of electronic properties of phenyl substituent probably due to the insignificance of the electronic effects (Anderson W K et al, *J. Med. Chem.* 1984, 27, 1321-1325; Anderson W K et al., *J. Med. Chem.* 1979, 22, 977-980).

In contrast with pyrrole derivatives, the C-5-phenyl and the pyrrole ring in 5-phenylpyrrolizine are coplanar. Studies on the structure-activity relationships of 5-phenylpyrrolizines revealed that compounds having electron-donating substituents on the phenyl ring were generally more toxic than compounds bearing electron-withdrawing substituents, while the in vivo antitumor activities were comparable or slightly less potent in compounds having an electron-donating substituent (Anderson W K et al., *J. Med. Chem.* 1983, 26, 1333-1338; Anderson W K et al., *J. Med. Chem.* 1982, 25, 84-86). These studies suggested that the lipophilicity of compound might also affect its antitumor potency.

It is accordingly a primary object of the invention to disclose a series of newly synthesized compounds that posses potent antitumor therapeutic efficacy. Specifically, the present inventors synthesized a series of bis(hydroxymethyl) of 8-H-3a-azacyclopenta[a]indene and 5,10-dihydropyrrolo[1,2-b]isoquinolines derivatives (Formula I and III, respectively) and their corresponding biscarbamates (Formula II and IV, respectively), which can be considered as "benzologues" of pyrrolizines, for antitumor studies.

These agents were subjected to antitumor studies. The results showed that these compounds could exhibit significant cytotoxicity in inhibiting various human tumor cell growth in vitro and could possess potent therapeutic efficacy in animal bearing human tumor xenografts (such as human breast carcinoma MX-1 and lung carcinoma HCT-116). The results demonstrated these compounds could possess potent antitumor therapeutic efficacy and have potential for clinical applications.

SUMMARY OF THE INVENTION

Provided herein is at least one chemical entity chosen from compounds of Formula I-IV:

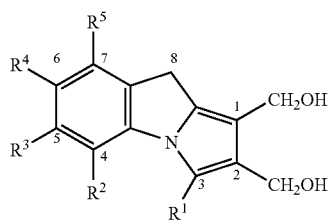

Formula I

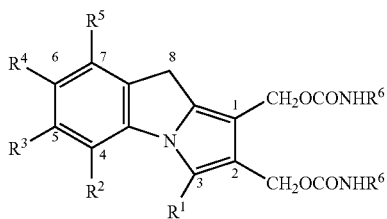

Formula II

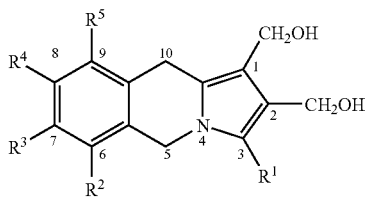

Formula III

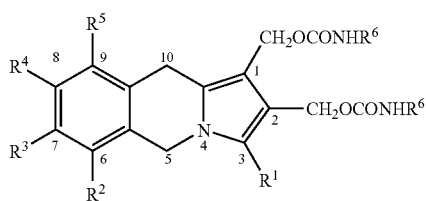

Formula IV

Wherein, $R^1$ is chosen from hydrogen, a $C_1$-$C_5$ linear or branched alkyl group, an aryl, a heteroaryl, and a benzyl, which may be unsubstituted or substituted;

$R^2$, $R^3$, $R^4$ and $R^5$ are independently chosen from hydrogen, $C_1$-$C_6$ alkyl, $OR^a$, halo, cyano, nitro, $NH_2$, $NHR^b$, $N(R^b)_2$, a $C_3$-$C_6$ cyclic alkylamino group, a methylenedioxy and ethylenedioxy group; wherein $R^a$ is chosen from hydrogen and $C_1$-$C_{10}$ alkyl, and $R^b$ is chosen from hydrogen and $C_1$-$C_{10}$ alkyl; and $R^6$ is chosen from a saturated or unsaturated, linear or branched, $C_1$-$C_5$ alkyl group, an optionally substituted phenyl group, and an optionally substituted benzyl group.

Also provided is a composition comprising at least one chemical compound described herein.

Also provided is a method of treating cancer comprising providing an effective amount of the compound disclosed herein and allowing the compound to treat the cancer.

Also provided is a method of inhibiting cancer cell growth comprising providing an effective amount of the compound disclosed herein and allowing the compound to inhibit cancer cell growth.

Also provided is a method of killing at least one cancer cell comprising providing an effective amount of the compound disclosed herein and allowing the compound to kill the cancer cell.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate several embodiments of the invention and together with the description, serve to explain the principles of the invention.

DESCRIPTION OF THE EMBODIMENTS

Figure 1:
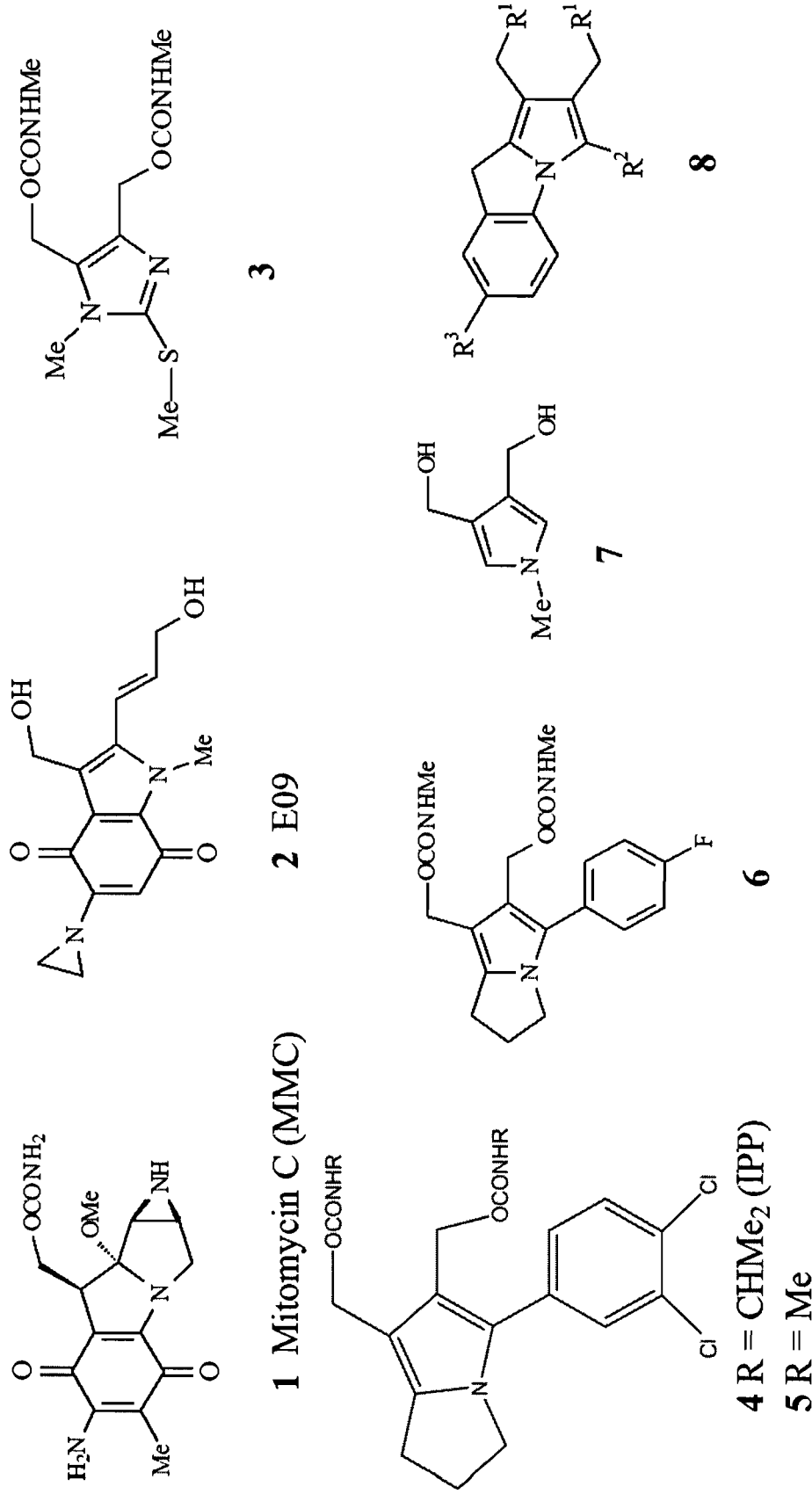
FIG. 1 shows chemical compounds discussed in the Background section.

Reference will now be made in detail to the present embodiment (exemplary embodiments) of the invention, examples of which are illustrated in the accompanying drawings. Wherever possible, the same reference numbers will be used throughout the drawings to refer to the same or like parts.

I. Compounds of Interest

The present application discloses compounds of Formula I-IV:

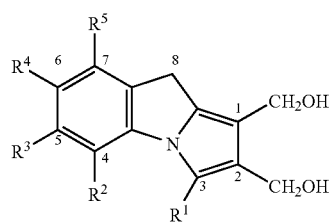

Formula I

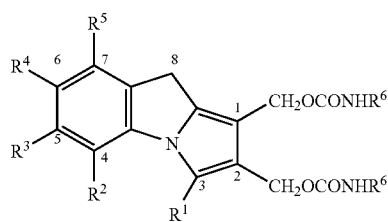

Formula II

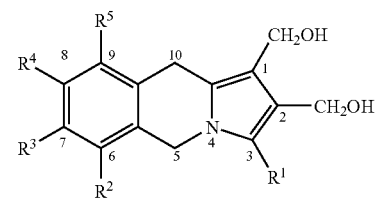

Formula III

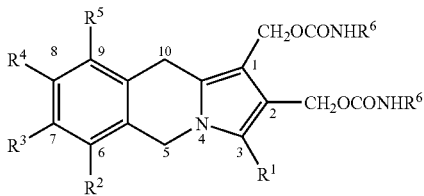

Wherein, $R^1$ is chosen from hydrogen, a $C_1$-$C_5$ linear or branched alkyl group, an aryl, a heteroaryl, and a benzyl, which may be unsubstituted or substituted;

$R^2$, $R^3$, $R^4$ and $R^5$ are independently chosen from hydrogen, $C_1$-$C_6$ alkyl, $OR^a$, halo, cyano, nitro, $NH_2$, $NHR^b$, $N(R^b)_2$, a $C_3$-$C_6$ cyclic alkylamino group or a methylenedioxy and ethylenedioxy group; wherein $R^a$ is chosen from hydrogen and $C_1$-$C_{10}$ alkyl, and $R^b$ is chosen from hydrogen and $C_1$-$C_{10}$ alkyl; and $R^6$ is chosen from a saturated or unsaturated, linear or branched, $C_1$-$C_5$ alkyl group, an optionally substituted phenyl group, and an optionally substituted benzyl group.

In one embodiment, examples of the compounds of Formula I may be chosen from:

(2-Hydroxymethyl-3-methyl-8H-3a-aza-cyclopenta[a]inden-1-yl)methanol;

(3-Ethyl-2-hydroxymethyl-8H-3a-aza-cyclopenta[a]inden-1-yl)methanol;

(2-Hydroxymethyl-3-propyl-8H-3a-aza-cyclopenta[a]inden-1-yl)methanol;

(2-Hydroxymethyl-3-isopropyl-8H-3a-aza-cyclopenta[a]inden-1-yl)methanol;

(2-Hydroxymethyl-3-butyl-8H-3a-aza-cyclopenta[a]inden-1-yl)methanol;

(2-Hydroxymethyl-3-phenyl-8H-3a-aza-cyclopenta[a]inden-1-yl)methanol;

(2-Hydroxymethyl-3-(2-methoxyphenyl)-8H-3a-aza-cyclopenta[a]inden-1-yl)methanol;

(2-Hydroxymethyl-3-(4-methoxyphenyl)-8H-3a-aza-cyclopenta[a]inden-1-yl)methanol;

(3-(3,4-Dimethoxyphenyl)-2-hydroxymethyl-8H-3a-aza-cyclopenta[a]inden-1-yl)methanol;

(3-(2,6-Dimethoxyphenyl)-2-hydroxymethyl-8H-3a-aza-cyclopenta[a]inden-1-yl)methanol;

(2-Hydroxymethyl-3-(3,4,5-trimethoxyphenyl)-8H-3a-aza-cyclopenta[a]inden-1-yl)-methanol;

(2-Hydroxymethyl-3-(4-methyl phenyl)-8H-3a-aza-cyclopenta[a]inden-1-yl)methanol;

(2-Hydroxymethyl-3-(4-nitrophenyl)-8H-3a-aza-cyclopenta[a]inden-1-yl)methanol;

(3-(4-Aminophenyl)-2-hydroxymethyl-8H-3a-aza-cyclopenta[a]inden-1-yl)methanol;

(3-(4-Flourophenyl)-2-hydroxymethyl-8H-3a-aza-cyclopenta[a]inden-1-yl)methanol;

(3-(4-Chlorophenyl)-2-hydroxymethyl-8H-3a-aza-cyclopenta[a]inden-1-yl)methanol;

(3-(3,4-Diflourophenyl)-2-hydroxymethyl-8H-3a-aza-cyclopenta[a]inden-1-yl)methanol;

(3-(3,4-Dichlorophenyl)-2-hydroxymethyl-8H-3a-aza-cyclopenta[a]inden-1-yl)methanol;

(2-Hydroxymethyl-6-methoxy-3-(4-methoxyphenyl)-8H-3a-aza-cyclopenta[a]inden-1-yl)methanol;

(2-Hydroxymethyl-6-nitro-3-(4-methoxyphenyl)-8H-3a-aza-cyclopenta[a]inden-1-yl)-methanol;

(6-Amino-2-hydroxymethyl-3-(4-methoxyphenyl)-8H-3a-aza-cyclopenta[a]inden-1-yl)methanol;

(2-Hydroxymethyl-6-methyl-3-(4-methoxyphenyl)-8H-3a-aza-cyclopenta[a]inden-1-yl)-methanol;

(6-Chloro-2-hydroxymethyl-3-methyl-8H-3a-aza-cyclopenta[a]inden-1-yl)methanol;

(6-Flouro-2-hydroxymethyl-3-methyl-8H-3a-aza-cyclopenta[a]inden-1-yl)methanol;

(5,6-dimethoxy-2-hydroxymethyl-3-(2-methoxyphenyl)-8H-3a-aza-cyclopenta[a]inden-1-yl)methanol;

(5,6-Methylenedioxy-2-hydroxymethyl-3-(2-methoxyphenyl)-8H-3a-aza-cyclopenta[a]inden-1-yl)methanol;

(5,6-Ethylenedioxy-2-hydroxymethyl-3-(2-methoxyphenyl)-8H-3a-aza-cyclopenta[a]inden-1-yl)methanol;

(2-hydroxymethyl-3-(2-methoxyphenyl)-6-pyrrolidi-1-nyl-8H-3a-aza-cyclopenta[a]inden-1-yl)methanol;

(2-hydroxymethyl-3-(2-methoxyphenyl)-6-morpholin-4-yl-8H-3a-aza-cyclopenta[a]inden-1-yl)methanol;

(2-hydroxymethyl-4,5,6-trimethoxy-3-methyl-8H-3a-aza-cyclopenta[a]inden-1-yl)methanol; and (6-dimethylamino-2-hydroxymethyl-3-methyl-8H-3a-aza-cyclopenta[a]inden-1-yl)methanol.

In one embodiment, examples of the compounds of Formula II may be chosen from:

Methylcarbamic acid 3-methyl-2-methylcarbamoyloxymethyl-8H-3a-aza-cyclopenta-[a]inden-1-ylmethyl ester;

Methylcarbamic acid 3-ethyl-2-methylcarbamoyloxymethyl-8H-3a-aza-cyclopenta-[a]inden-1-ylmethyl ester;

Methylcarbamic acid 3-propyl-2-methylcarbamoyloxymethyl-8H-3a-aza-cyclopenta[a]inden-1-ylmethyl ester;

Methylcarbamic acid 3-butyl-2-methylcarbamoyloxymethyl-8H-3a-aza-cyclopenta[a]inden-1-ylmethyl ester;

Methylcarbamic acid 3-isopropyl-2-methylcarbamoyloxymethyl-8H-3a-aza-cyclopenta[a]inden-1-yl-methyl ester;

Methyl-carbamic acid 2-methylcarbamoyloxymethyl-3-phenyl-8H-3a-aza-cyclopenta[a]inden-1-ylmethylester;

Methylcarbamic acid 3-(4-flourophenyl)-2-methylcarbamoyloxymethyl-8H-3a-aza-cyclopenta[a]inden-1-ylmethyl ester;

Methylcarbamic acid 3-(4-chlorophenyl)-2-methyl-carbamoyloxymethyl-8H-3a-aza-cyclopenta[a]inden-1-ylmethyl ester;

Methylcarbamic acid 3-(3,4-diflourophenyl)-2-methylcarbamoyloxymethyl-8H-3a-aza-cyclopenta[a]inden-1-ylmethyl ester;

Methylcarbamic acid 3-(4-methoxy-phenyl)-2-methylcarbamoyloxymethyl-8H-3a-azacyclopenta[a]inden-1-ylmethyl ester;

Methylcarbamic acid 3-(2-methoxyphenyl)-2-methylcarbamoyloxymethyl-8H-3a-aza-cyclopenta[a]inden-1-ylmethyl ester;

Methylcarbamic acid 3-(3,4-dimethoxyphenyl)-2-methylcarbamoyloxymethyl-8H-3a-aza-cyclopenta[a]inden-1-ylmethyl ester;

Methylcarbamic acid 3-(2,6-dimethoxyphenyl)-2-methylcarbamoyloxymethyl-8H-3a-aza-cyclopenta[a]inden-1-ylmethyl ester;

Methylcarbamic acid 3-(3,4,5-trimethoxyphenyl)-2-methylcarbamoyloxymethyl-8H-3a-aza-cyclopenta[a]inden-1-ylmethyl ester;

Methylcarbamic acid 6-methoxy-3-(4-methoxyphenyl)-2-methylcarbamoyloxy-methyl-8H-3a-aza-cyclopenta[a]inden-1-ylmethyl ester;
Methylcarbamic acid 3-(4-methoxyphenyl)-2-methylcarbamoyloxymethyl-6-pyrrolidin-1-yl-8H-3a-aza-cyclopenta[a]inden-1-ylmethyl ester;
Methylcarbamic acid 3-(4-methoxyphenyl)-2-methylcarbamoyloxymethyl-6-piperidin-1-yl-8H-3a-aza-cyclopenta[a]inden-1-ylmethyl ester;
Methylcarbamic acid 3-(4-nitrophenyl)-2-methylcarbamoyloxymethyl-8H-3a-aza-cyclopenta[a]inden-1-ylmethyl ester;
Methylcarbamic acid 3-(4-aminophenyl)-2-methylcarbamoyloxymethyl-8H-3a-aza-cyclopenta[a]inden-1-ylmethyl ester;
Methylcarbamic acid 5,6-methylenedioxy-2-methylcarbamoyloxymethyl-3-(2-methoxyphenyl)-8H-3a-aza-cyclopenta[a]inden-1-ylmethyl ester;
Methylcarbamic acid 5,6-ethylenedioxy-2-methylcarbamoyloxymethyl-3-(2-methoxyphenyl)-8H-3a-aza-cyclopenta[a]inden-1-ylmethyl ester;
Ethylcarbamic acid 2-ethylcarbamoyloxymethyl-3-(4-methoxy-phenyl)-8H-3a-aza-cyclopenta[a]inden-1-ylmthyl ester;
Propylcarbamic acid 3-methyl-2-propylcarbamoyloxymethyl-8H-3a-aza-cyclopenta[a]inden-1-ylmethyl ester;
Isopropylcarbamic acid 2-isopropylcarbamoyloxymethyl-3-methyl-8H-3a-aza-cyclopenta[a]inden-2-ylmethyl ester;
Isobutylcarbamic acid 2-isobutylcarbamoyloxymethyl-3-methyl-8H-3a-aza-cyclopenta[a]inden-2-ylmethyl ester; and
Phenylcarbamic acid 3-methyl-2-phenylcarbamoyloxymethyl-8H-3a-aza-cyclopenta[a]inden-1-ylmethyl ester.

In one embodiment, examples of the compounds of Formula III may be selected from:
(1-Hydroxymethyl-3-methyl-5,10-dihydro-pyrrolo[1,2-b]isoquinolin-2-yl)methanol;
(3-Ethyl-1-hydroxymethyl-5,10-dihydro-pyrrolo[1,2-b]isoquinolin-2-yl)methanol;
(1-Hydroxymethyl-3-phenyl-5,10-dihydro-pyrrolo[1,2-b]isoquinolin-2-yl)methanol;
(3-(4-chlorophenyl)-1-hydroxymethyl-5,10-dihydro-pyrrolo[1,2-b]isoquinolin-2-yl)-methanol;
[3-(4-flourophenyl)-1-hydroxymethyl-5,10-dihydro-pyrrolo[1,2-b]isoquinolin-2-yl]-methanol;
[3-(3,4-diflourophenyl)-1-hydroxymethyl-5,10-dihydro-pyrrolo[1,2-b]isoquinolin-2-yl]-methanol;
(1-Hydroxymethyl-3-(2-methoxyphenyl)-5,10-dihydro-pyrrolo[1,2-b]isoquinolin-2-yl)methanol;
(1-Hydroxymethyl-3-(4-methoxyphenyl)-5,10-dihydro-pyrrolo[1,2-b]isoquinolin-2-yl)methanol; and
[3-(3,4-dimethoxyphenyl)-1-hydroxymethyl-5,10-dihydro-pyrrolo[1,2-b]isoquinolin-2-yl]methanol.

In one embodiment, examples of compounds of Formula IV may be selected from:

Methylcarbamic acid 3-methyl-2-methylcarbamoyloxymethyl-5,10-dihydropyrrolo-[1,2-b]isoquinolin-1-ylmethyl ester;
Methylcarbamic acid 3-ethyl-2-methylcarbamoyloxymethyl-5,10-dihydropyrrolo-[1,2-b]isoquinolin-1-ylmethyl ester;
Methylcarbamic acid 2-methylcarbamoyloxymethyl-3-phenyl-5,10-dihydropyrrolo-[1,2-b]isoquinolin-1-ylmethyl ester;
Methyl-carbamic acid 3-(4-chlorophenyl)-2-methylcarbamoyloxymethyl-5,10-dihydropyrrolo[1,2-b]isoquinolin-1-ylmethyl ester;
Methylcarbamic acid 3-(4-flourophenyl)-2-methylcarbamoyloxymethyl-5,10-dihydropyrrolo[1,2-b]isoquinolin-1-ylmethyl ester;
Methylcarbamic acid 3-(3,4-diflourophenyl)-2-methylcarbamoyloxymethyl-5,10-dihydropyrrolo[1,2-b]isoquinolin-1-ylmethyl ester;
Methylcarbamic acid 3-(2-methoxyphenyl)-2-methylcarbamoyloxymethyl-5,10-dihydropyrrolo[1,2-b]isoquinolin-1-ylmethyl ester;
Methylcarbamic acid 3-(4-methoxyphenyl)-2-methylcarbamoyloxymethyl-5,10-dihydropyrrolo[1,2-b]isoquinolin-1-ylmethyl ester;
Methylcarbamic acid 3-(3,4-dimethoxyphenyl)-2-methylcarbamoyloxymethyl-5,10-dihydropyrrolo[1,2-b]isoquinolin-1-ylmethyl ester;
Propylcarbamic acid 3-methyl-2-propylcarbamoyloxymethyl-5,10-dihydropyrrolo-[1,2-b]isoquinolin-1-ylmethyl ester;
Propylcarbamic acid 3-ethyl-2-propylcarbamoyloxymethyl-5,10-dihydropyrrolo-[1,2-b]isoquinolin-1-ylmethyl ester;
Propylcarbamic acid 3-phenyl-2-propylcarbamoylmethyl-5,10-dihydropyrrolo-[1,2-b]isoquinolin-1-ylmethyl ester;
Propylethylcarbamic acid 3-(4-chlorophenyl)-2-propylcarbamoyloxymethyl-5,10-dihydropyrrolo[1,2-b]isoquinolin-1-ylmethyl ester;
Propylcarbamic acid 3-(4-flourophenyl)-2-propylcarbamoyloxymethyl-5,10-dihydropyrrolo[1,2-b]isoquinolin-1-ylmethyl ester;
Propylcarbamic acid 3-(3,4-diflourophenyl)-2-propylcarbamoyloxymethyl-5,10-dihydropyrrolo[1,2-b]isoquinolin-1-ylmethyl ester;
Propylcarbamic acid 3-(4-methoxyphenyl)-2-propylcarbamoyloxymethyl-5,10-dihydropyrrolo[1,2-b]isoquinolin-1-ylmethyl ester; and
Propylcarbamic acid 3-(3,4-dimethoxyphenyl)-2-propylcarbamoyloxymethyl-5,10-dihydropyrrolo[1,2-b]isoquinolin-1-ylmethyl ester.

In one embodiment, it is expected that the newly synthesized compounds can undergo $S_N1$ electrophilic reaction to cross-link DNA via a similar mechanism of action as that of pyrroles or pyrrolizines (Scheme 1).

Scheme 1. The proposed mechanism of DNA bialklation by cyclopenta[a] indene

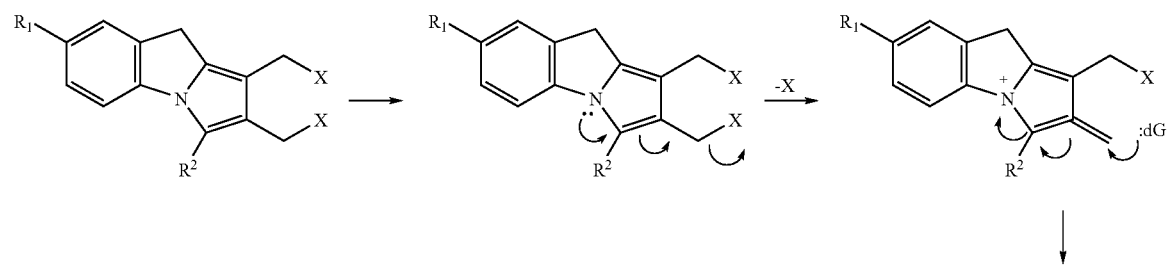

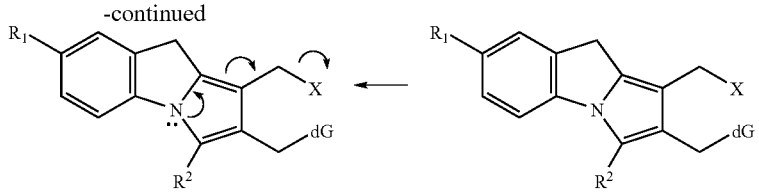

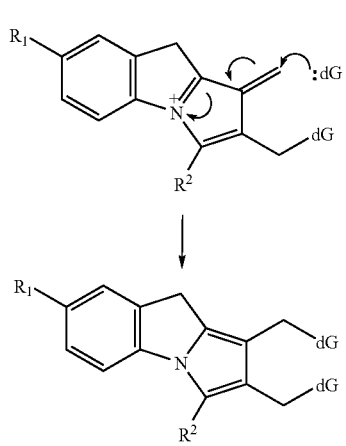

"Optionally" means that the subsequently described event or circumstance may, but need not occur, and that the description includes instances where the event or circumstance occurs and instances in which the event does not.

"Substituted" refers to one or more hydrogen atoms are each independently replaced with the same or different substituents.

The term "Alkyl" encompasses straight chain and branched chain having the indicated number of carbon atoms. The term "Alkyl" also intended to include groups having any degree or level of saturation, i.e., groups having exclusively single carbon-carbon bonds, groups having one ore more double carbon-carbon bonds, groups having one or more triple carbon-carbon bonds, and groups having mixtures of single, double and triple carbon-carbon bonds. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. When an alkyl having a specific number of carbon is names, all geometric isomers having that number of carbons are intend to be encompassed. For example, "butyl" is meant to include n-butyl, sec-butyl, isobutyl and t-butyl. The alkyl group may be substituted or unsubstituted. When substituted, each substituent can be independently chosen from, for instance, halogen, -hydroxy, alkoxy, —COR', —COOR', OCOR', —CONRR', —RNCOR', —NRR', —CN, —NO$_2$, —SR', —SOR', —SO$_2$R', —SO$_2$OR', —SO$_2$NRR', ammonium, lower alkyl, lower alkenyl, lower alkynyl, cycloalkyl, heteroalicycle, heteroaryl and aryl. R and R' are independently H, alkyl, or aryl, wherein alkyl or aryl may be further substituted.

"Aryl" refers to an all-carbon monocyclic or fused-ring polycyclic (i.e. rings which share adjacent pairs of carbon atoms). Examples of hydrocarbon aryl moieties include substituted or unsubstituted phenyl, naphthyl, pyrenyl, anthryl, phenanthryl, and benzyl. The aryl group may be substituted or unsubstituted. When substituted, one or more substituents can be independently chosen from, for example, from $C_1$-$C_6$ alkyl, OR$^a$; halo, cyano, nitro, NH$_2$, NHR$^b$, N(R$^b$)$_2$, a $C_3$-$C_6$ cyclic alkylamino group, or a methylenedioxy or ethylenedioxy group; wherein R$^a$ is hydrogen or $C_1$-$C_{10}$ alkyl, and R$^b$ is hydrogen or $C_1$-$C_{10}$ alkyl. The number of the substituent is not limited and can be from 1 to 5.

The term "heteroaryl" refers to a monocyclic or fused ring (i.e., rings which share an adjacent pair of atoms) containing one or more heteroatoms chosen from carbon, oxygen, nitrogen and sulfur. Examples of heteroaryl moieties include furyl, pyrrolyl, thienyl, oxazoyl, imidazoyl, thiazoyl, pyridyl, pyrimidinyl, quinazolinyl and indolyl. The heteroaryl group may be substituted or unsubstituted. When substituted, one or more substituent can be independently chosen from, for example, from $C_1$-$C_6$ alkyl, OR$^a$; halo, cyano, nitro, NH$_2$, NHR$^b$, N(R$^b$)$_2$, a $C_3$-$C_6$ cyclic alkylamino group, or a methylenedioxy or ethylenedioxy group; wherein R$^a$ is hydrogen or $C_1$-$C_{10}$ alkyl, and R$^b$ is hydrogen or $C_1$-$C_{10}$ alkyl. The number of the substituent in not limited and can be from 1 to 5.

The term "halo" refers to any radical of fluorine, chlorine, bromine and iodine.

II. Synthesis

The compounds disclosed herein can be synthesized using conventional techniques. For example, these compounds can be conveniently synthesized from readily available starting materials using standard organic chemistry synthesis methods, including those methods illustrated in the schemes and the examples herein.

As a non-limiting example, the synthesis method of the compounds of Formulae I-IV includes starting with a compound of Formula V, VI, VII, VIII, or IX:

Formula V

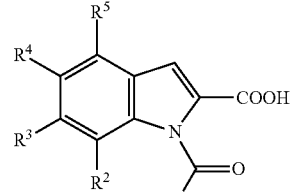

Formula VI

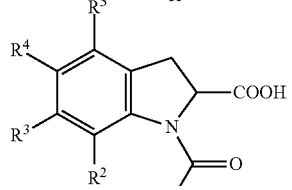

Formula VII

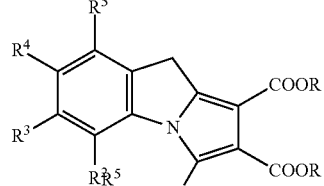

Formula VIII

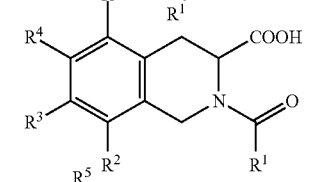

Formula IX

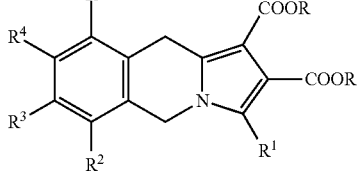

wherein $R^1$, $R^2$, $R^3$, $R^4$, $R^5$ and $R^6$ are defined as above

In one embodiment, compounds of Formulae I and II can be synthesized as shown in Scheme 2. Treatment of the commercially available indoline-2-carboxylic acid (9) with appropriate acid chlorides (such as alkylcarbonyl or arylcarbonyl chlorides) or acid anhydrides (such as alkyl- or arylcarboxylic acid anhydrides) in the presence of a base (inorganic such as $Na_2CO_3$, $K_2CO_3$, or NaH, etc or organic bases such as pyridine, triethylamine, 4-N,N-dimehtylaminopyridine, etc.) can give N-acyl derivatives (10). Alternatively, compounds (10) can be obtained starting from various indol-2-carboxylic acids (11) via N-acylation by treating it with appropriate acid chlorides or acid anhydrides in the presence of base, followed with catalytic hydrogenation ($PtO/H_2$/ EtOH or other reducing agents). Reaction of compound 10 with dimethyl acetylenedicarboxylate (DMAD) in acetic anhydride by heating can produce 8H-3a-aza-cyclopenta[a] indene-1,2-dicarboxylic acid dimethyl ester (13), which can be further reduced to give the C3 substituted (2-hydroxymethyl-8H-3a-aza-cyclopenta[a]inden-1-yl)methanol derivatives (14, compounds of Formula I) by treating it with $LiAlH_4$ in a appropriate solvent such as THF, ether or $CH_2Cl_2$. Treatment of 14 with various alkyl-, phenyl- or benzylisocyantes in the presence of base (such as triethylamine or pyridine) can yield the desired bis(carbamates) 15 (compounds of Formula II).

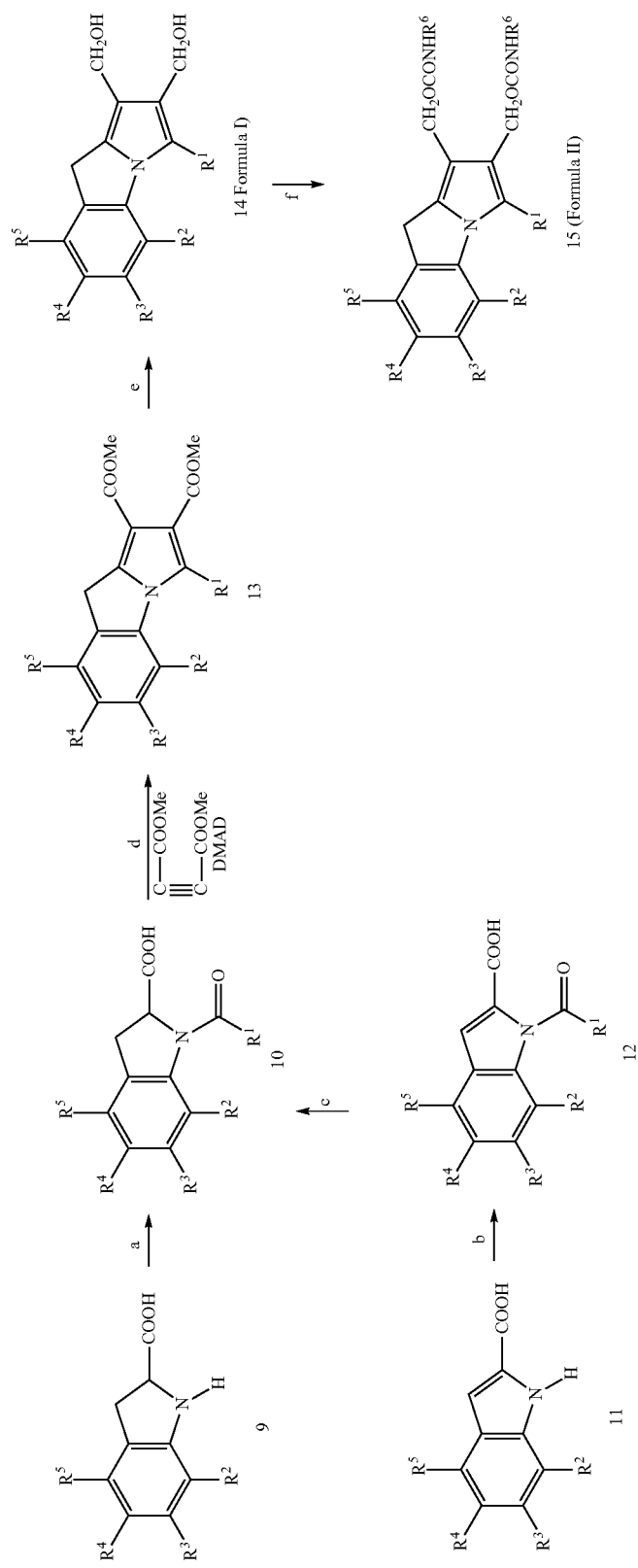
Scheme 2
Optional reaction conditions: a: acid chloride/Et₃N/dry CH₂Cl₂, 0-25° C., 3 h; b: acid chloride/Et₃N/dry CH₂Cl₂/ DMAP, 0-25° C., 5 h; c: PtO₂/H₂/EtOH, 14 h; d: dimethyl acetylenedicarboxylate/AC₂O, 120° C.; e: LiAlH₄/CH₂Cl₂/EtO₂, 0° C., 15 min.
f: R⁶NCO/CH₂Cl₂/Et₃N, rt, 4-5 h.

By following a similar procedure as described above for the synthesis of compounds of Formula I and Formula II, compounds of Formulae III and IV can be prepared by another non-limiting example of the present invention as shown in Scheme 3. Various substituted D,L-phenylalanines (16) can be converted into isoquinoline-3-carboxylic acids (17), which can be N-acylated by treating with various acid chlorides or acid anhydrides in the presence of a base to give N-acyl-2,3-dihydro-1H-indole-2-carboxylic acids (18). 1,3-Dipolar cyclization of compound 18 with DMAD can yield C3 substituted 8H-3a-aza-cyclopenta[a]indene-1,2-dicarboxylic acid di-esters (19), which can be then converted into the desired C3 substituted 2-hydroxymethyl-5,10-dihydropyrrolo[1,2-b]isoquinolin-1-yl]methanol derivatives (20, compounds of Formula III) by treating with $LiAlH_4$ or other reducing agents in an appropriate solvent such as THF, ether, or $CH_2Cl_2$. Treatment of compound 20 with a variety of isocyanates in the presence of a base (such as triethylamine or pyridine) can yield the desired bis(carbamates) 21 (compounds of Formula IV).

rian cancer, uterine body cancer, cervical cancer, oral cancer, skin cancer, brain cancer, lymphoma, and leukemia. It also includes drug resistant cancer (including but not limited to multidrug resistant cancer).

As used herein, treatment of cancer includes treatment of cancer cells, including cells afflicted by any one of the above-identified conditions. Thus, the term "cancer cells" as provided herein, includes cells afflicted by any one of the above identified conditions.

The chemical compounds disclosed herein can also be used to treat cellular proliferation diseases. Such disease states which can be treated by the chemical entities provided herein include, but are not limited to, cancer, autoimmune disease, fungal disorders, arthritis, graft rejection, inflammatory bowel disease, cellular proliferation induced after medical procedures, including, but not limited to, surgery, angioplasty, and the like. Treatment includes inhibiting cellular proliferation. It is appreciated that in some cases the cells may not be in an abnormal state and still require treatment. Thus, in some embodiments, the invention herein includes applica-

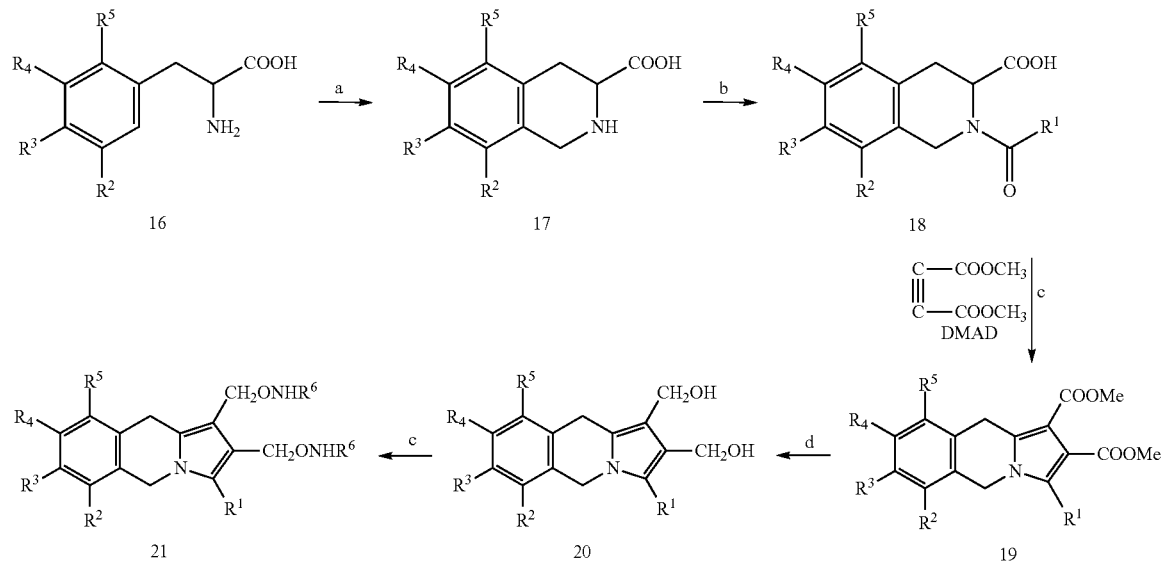

Scheme 3

Optional reaction conditions: a: formaldehyde or polyformarmaldehyde/conc. HCl, reflux;
b: $(RCO)_2O$ or RCOCl/base; c: $DMAD/Ac_2O$, 40-120° C.; d: $LiAlH4/THF$, ether, or $CH_2Cl_2$, etc, room tempt.; e: varoius isocyanates ($R^6NCO$)/base.

III. Clinical Applications

A. Diseases

The chemical entities, pharmaceutical formulations and methods provided herein are deemed useful for the treatment of cancer. "Cancer" is any abnormal cell or tissue growth, for example, a tumor, whether malignant, pre-malignant, or non-malignant. It is characterized by uncontrolled proliferation of cells that may or may not invade the surrounding tissue and, hence, may or may not metastasize to new body sites. Cancer encompasses carcinomas, which are cancers of epithelial cells; carcinomas include squamous cell carcinomas, adenocarcinomas, melanomas, and hepatomas. Cancer also encompasses sarcomas, which are tumors of mesenchymal origin; sarcomas include osteogenic sarcomas, leukemias, and lymphomas. Cancers may involve one or more neoplastic cell type. The term cancer includes, as non-limiting examples, lung cancer, colon cancer, colorectal cancer, breast cancer, prostate cancer, liver cancer, pancreatic cancer, bladder cancer, gastric cancer, renal cancer, salivary gland cancer, ovation to cells or individuals afflicted or subject to impending affliction with any one of these disorders or states.

In another embodiment, the chemical compounds disclosed herein can be used to treat cells that exhibit drug resistance. The term "drug resistance" refer to the reduction in effectiveness of a drug in curing a disease, killing a cancer cell, or inhibiting, suppressing, or improving particular cellular function. The term "drug resistant cancer cells" encompass cancer cells that are resistant to one or more drug. The drugs referred to herein include, but are not limited to, certain commonly used chemotherapy drugs such as taxol, vinblastine, carboplatin, cisplatin, cylcophosphamide, docetaxel, doxorubicin, erlotinib, etoposide, fluorouracil, gemcitabine, imatinib mesylate, irinotecan, methotrexate, sorafinib, sunitinib, and topotecan.

B. Routes of Administration

Administration of the compounds of formula I-IV disclosed herein can be achieved in various ways, including oral, buccal, nasal, rectal, parenteral, intraperitoneal, intradermal, transdermal, subcutaneous, intravenous, intra-arterial, intracardiac, intraventricular, intracranial, intratracheal, and intrathecal administration, etc., or otherwise by implantation or inhalation. Further as non-limiting examples, the compound described herein can be administered via oral, intravenous or intraperitoneal injection, or topical route. Thus, the subject compositions can be formulated into preparations in solid, semi-solid, liquid, or gaseous forms, such as tablets, capsules, powders, granules, ointments, solutions, suppositories, injections, inhalants and aerosols. The following methods and excipients are merely exemplary and are in no way limiting.

When a therapeutically effective amount of the disclosed compounds is administered orally, the binding agent may be in the form of a tablet, capsule, powder, solution or elixir. When administered in tablet form, the pharmaceutical composition of the invention may additionally contain a solid carrier such as a gelatin or an adjuvant. The tablet, capsule, and powder contain from about 5 to 95% binding agent, and in other embodiments from about 25 to 90% binding agent. Examples are sucrose, kaolin, glycerin, starch dextrins, sodium alginate, carboxymethylcellulose and ethyl cellulose. Coloring and/or flavoring agents may be present. A coating shell may be employed. When administered in liquid form, a liquid carrier such as water, petroleum, oils of animal or plant origin such as peanut oil, mineral oil, soybean oil, or sesame oil, or synthetic oils may be added. The liquid form of the pharmaceutical composition may further contain physiological saline solution, dextrose or other saccharide solution, or glycols such as ethylene glycol, propylene glycol or polyethylene glycol. When administered in liquid form, the pharmaceutical composition contains from about 0.5 to 90% by weight of the binding agent, for example, from 1 to 50% of the binding agent.

When a therapeutically effective amount of the disclosed compounds is administered by intravenous, cutaneous or subcutaneous injection, binding agent may be in the form of a pyrogen-free, parenterally acceptable aqueous solution. The preparation of such parenterally acceptable protein solutions, having due regard to pH, isotonicity, stability, and the like, is within the skill in the art. In some embodiments, pharmaceutical composition for intravenous, cutaneous, or subcutaneous injection may contain, in addition to binding agent an isotonic vehicle such as Sodium Chloride Injection, Ringer's Injection, Dextrose Injection, Dextrose and Sodium Chloride Injection, Lactated Ringer's Injection, or other vehicle as known in the art. The pharmaceutical composition of the present invention may also contain stabilizers, preservatives, buffers, antioxidants, or other additive known to those of skill in the art.

Solutions or suspensions used for parenteral, intradermal, or subcutaneous application can optionally include any of the following components: a sterile diluent, such as water for injection, saline solution, fixed oil, polyethylene glycol, glycerine, propylene glycol or other synthetic solvent; antimicrobial agents, such as benzyl alcohol and methyl parabens; antioxidants, such as ascorbic acid and sodium bisulfite; chelating agents, such as ethylenediaminetetraacetic acid (EDTA); buffers, such as acetates, citrates and phosphates; and agents for the adjustment of tonicity such as sodium chloride or dextrose. Parenteral preparations can be enclosed in ampoules, disposable syringes or single or multiple dose vials made of glass, plastic or other suitable material.

In instances in which the compounds exhibit insufficient solubility, methods for solubilizing compounds may be used. Such methods are known to those of skill in this art, and include, but are not limited to, using co-solvents, such as dimethylsulfoxide (DMSO), using surfactants, such as TWEEN®, or dissolution in aqueous sodium bicarbonate.

In practicing the method of treatment or use of the present invention, a therapeutically effective amount of the disclosed compounds is administered to a subject, e.g., mammal such as a human or nonhuma mammal, for example, dogs, cats, pigs, cows, sheep, goats, horses, rats, or mice. As used herein, the term "therapeutically effective amount" means the total amount of each active component of the pharmaceutical composition or method that is sufficient to show a meaningful patient benefit, e.g., amelioration of symptoms of, healing of, or increase in rate of healing of such conditions. When applied to an individual active ingredient, administered alone, the term refers to that ingredient alone. When applied to a combination, the term refers to combined amounts of the active ingredients that result in the therapeutic effect, whether administered in combination, serially or simultaneously.

C. Pharmaceutical Compositions

The compounds disclosed in the present invention may be used as a pharmaceutical composition when combined with a pharmaceutically acceptable carrier. Such a composition may contain, in addition to the compounds disclosed herein, various diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier may depend on the route of administration.

In the compositions, effective concentrations of the compounds described herein is mixed with a suitable pharmaceutical carrier or vehicle. Typically, the compositions are formulated for single dosage administration. To formulate a composition, the weight fraction of compound is dissolved, suspended, dispersed or otherwise mixed in a selected vehicle at an effective concentration such that the treated condition is relieved or ameliorated. Pharmaceutical carriers or vehicles suitable for administration of the compounds provided herein include any such carriers known to those skilled in the art to be suitable for the particular mode of administration.

Parenteral administration of the compositions includes intravenous, subcutaneous and intramuscular administrations. Preparations for parenteral administration include sterile solutions ready for injection, sterile dry soluble products, such as lyophilized powders, ready to be combined with a solvent just prior to use, including hypodermic tablets, sterile suspensions ready for injection, sterile dry insoluble products ready to be combined with a vehicle just prior to use and sterile emulsions. The solutions may be either aqueous or nonaqueous.

Parenteral administration, generally characterized by injection, either subcutaneously, intramuscularly or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol or ethanol. In addition, if desired, the pharmaceutical compositions to be administered may also contain minor amounts of non-toxic auxiliary substances such as wetting or emulsifying agents, pH buffering agents, stabilizers, solubility enhancers, and other such agents, such as for example, sodium acetate, sorbitan monolaurate, triethanolamine oleate and cyclodextrins.

If administered intravenously, suitable carriers include physiological saline or phosphate buffered saline (PBS), and solutions containing thickening and solubilizing agents, such as glucose, polyethylene glycol, and polypropylene glycol and mixtures thereof.

It is especially advantageous to formulate compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The unit-dose parenteral preparations are packaged in an ampoule, a vial or a syringe with a needle. Preparations for parenteral administration should be sterile, as is known and practiced in the art.

The concentration of the pharmaceutically active compound is adjusted so that an injection provides an effective amount to produce the desired pharmacological effect. The exact dose depends on the age, weight and condition of the patient or animal as is known in the art.

The amount of the disclosed compounds in the pharmaceutical composition of the present invention may depend upon the nature and severity of the condition being treated, and on the nature of prior treatments that the patient has undergone, and patient's age and sex. Ultimately, the attending physician may decide the amount of active ingredient with which to treat each individual patient. Initially, the attending physician may administer low doses of active ingredient and observe the patient's response. Larger doses of active ingredient may be administered until the optimal therapeutic effect is obtained for the patient, and at that point the dosage is not generally increased further. In addition, the dosage amount useful to treat, prevent, inhibit or alleviate conditions will vary with the severity of the condition to be treated and the route of administration. The dose and dose frequency will also vary according to age, body weight, response and past medical history of the individual human patient. Dosages for non-human patients can be adjusted accordingly by one skilled in the art. It is contemplated that the various pharmaceutical compositions used to practice the method of the present invention may contain about 100 ng to about 100 mg compounds of formula I-IV per kg body weight per day. Examples of dosage ranges that can be administered to a subject can be chosen from: 1 µg/kg to 10 mg/kg, 1 µg/kg to 5 mg/kg, 10 µg/kg to 10 mg/kg, 10 µg/kg to 5 mg/kg, 100 µg/kg to 50 mg/kg, 100 µg/kg to 5 mg/kg, 500 µg/kg to 25 mg/kg, 500 µg/kg to 10 mg/kg, 500 µg/kg to 5 mg/kg, and 500 µg/kg to 2.5 mg/kg. For example, the daily dose can be chosen from 0.5 mg to 1000 mg per day, 1 mg to 200 mg per day, 2 mg to 500 mg per day, 10 mg to 50 mg per day, 100 mg to 2 g per day, 40 mg to 2 g per day, 40 mg to 200 mg per day. Specific dosages include all of the endpoints listed above.

The duration of therapy using the pharmaceutical composition of the present invention may vary, depending on the severity of the disease being treated and the condition and potential idiosyncratic response of each individual patient. Therapy may also be conducted in cycles with the patient receiving therapy for a period of time and then having a rest or recovery period before resuming therapy again. A cycle phase (of either treatment or rest, in any combination) may comprise one week, two weeks, three weeks, one month, or longer. In one embodiment, in is contemplated that the invented compound is administered via an intravenous injection three times a day until the condition is improved. Therapy may be conducted multiple times a day (such as four times a day, three times a day, twice a day), once a day, several times a week (four times a week, three times a week, twice a week), or once a week, or even less frequent intervals if the patients condition is improving and maintenance therapy is desired. In another embodiment, the invented compound is administered in conjunction with other treatments such as irradiation, hormone therapy, chemotherapy, and/or surgery. By in conjunction with, the therapies do not need to occur at the same time, but can be in succession, or alternating with each other and/or periods of rest and recovery.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Data obtained from the cell culture assays and animal studies can be used in evaluating a range of dosage for use in humans. The dosage of such compounds may lie within a range of circulating concentrations that include the $ED_{50}$ with little or no toxicity. The dosage may vary within this range depending upon the dosage form employed and the route of administration utilized. The therapeutically effective dose of compounds of Formula I-IV can be estimated initially from cell culture assays. A dose may be formulated in animal models to achieve a circulating plasma concentration range that includes the $IC_{50}$ (i.e., the concentration of the test compound which achieves a half-maximal inhibition of symptoms or which inhibit cancer cell growth by 50%) as determined in cell culture. Levels in plasma may be measured, for example, by high performance liquid chromatography. The effects of any particular dosage can be monitored by a suitable bioassay.

C. Treatment Schemes

The composition comprising at least one compounds of Formula I-IV of the present invention can be used individually or in combination and with other treatments, such as radiation therapy, immunotherapy, monoclonal antibody therapy, hormonal therapy, chemotherapy using other agents, and surgery.

In one embodiment, the present invention can be useful in combination with known therapeutic agents and anti-cancer agents. A person skilled in the art would be able to discern which combinations of agents would be useful based on the particular characteristics of the drugs and the cancer involved. Such anti-cancer agents include, but are not limited to, cytostatic/cytotoxic agents, anti-proliferative agents, cell cycle checkpoint inhibitors, angiogenesis inhibitors, monoclonal antibody targeted therapeutic agents, tyrosine kinase inhibitors, serine-threonine kinase inhibitors, histone deacetylase inhibitors, heat shock protein inhibitors, and farnesyl transferase inhibitors. The present invention can be useful in combination with radiation therapy.

The compounds disclosed herein can be useful, alone or in combination with other drugs or treatments, for any stage of cancer treatment such as neoadjuvant chemotherapy (preoperative treatment), adjuvant chemotherapy (postoperative treatment), or palliative chemotherapy. In another embodiment, the compounds disclosed herein can be used for the treatment of pre-malignant lesions, such as a chemoprevention therapy.

The terms "subject," "individual," "host," and "patient" are used interchangeably herein to refer to a living animal, including a human and a non-human animal. The subject may be a mammal, such as a human or non-huma mammal, for example, dogs, cats, pigs, cows, sheep, goats, horses, rats, and mice. The term "subject" does not preclude individuals that are entirely normal with respect to a disease, or normal in all respects.

The term "treatment," as used herein, covers any administration or application of remedies for disease in a mammal, including a human, and includes inhibiting the disease, arresting its development, or relieving the disease, for example, by causing regression, or restoring or repairing a lost, missing, or defective function; or stimulating an inefficient process. The term includes obtaining a desired pharmacologic and/or physiologic effect, covering any treatment of a pathological condition or disorder in a mammal, including a human. The effect may be prophylactic in terms of completely or partially preventing a disorder or symptom thereof and/or may be therapeutic in terms of a partial or complete cure for a disorder and/or adverse effect attributable to the disorder. Thus, the invention provides both treatment and prophylaxis. It includes (1) preventing the disorder from occurring or recurring in a subject who may be predisposed to the disorder but is not yet symptomatic, (2) inhibiting the disorder, such as arresting its development, (3) stopping or terminating the disorder or at least symptoms associated therewith, so that the host no longer suffers from the disorder or its symptoms, such as causing regression of the disorder or its symptoms, for example, by restoring or repairing a lost, missing or defective function, or stimulating an inefficient process, or (4) relieving, alleviating, or ameliorating the disorder, or symptoms associated therewith, where ameliorating is used in a broad sense to refer to at least a reduction in the magnitude of a parameter, such as inflammation, pain, and/or tumor size.

The term "therapeutically effective amount" means the amount of the subject compound that may elicit a desired response, for example, a biological or medical response of a tissue, system, animal, or human that is sought, for example, by a researcher, veterinarian, medical doctor, or other clinician.

"Disease" refers to any condition, infection, disorder, or syndrome that requires medical intervention or for which medical intervention is desirable. Such medical intervention can include treatment, diagnosis, and/or prevention.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

EXAMPLES

Example 1

Synthesis of (2-hydroxymethyl-3-methyl-8h-3a-aza-cyclopenta[a]inden-1-yl)-methanol (DA-1090)

Step 1: Preparation of 3-methyl-8h-3a-aza-cyclopenta[a]indene-1,2-dicarboxylic acid dimethyl ester A mixture of indoline 2-carboxylic acid (10.60 g, 65 mmol) and dimethyl acetylenedicarboxylate (9.24 g, 80 mmol) in acetic anhydride (110 mL) was stirred in a flask equipped with a reflux condenser and a gas bubbler to monitor carbon dioxide evolution during the reaction. The mixture was heated to 120° C. where carbon dioxide evolution was most intense. The temperature was maintained until gas evolution had ceased (ca. 10 h). The dark solution was concentrated in vacuo and the solid residue was crystallized from methanol to yield 3-methyl-8H-3a-aza-cyclopenta[a]indene-1,2-dicarboxylic acid dimethyl ester, 14.40 g (78%): mp 162-164° C.; $^1$H NMR (DMSO-d$_6$) δ 2.74 (3H, s, Me), 3.85 and 3.89 (each 3H, s, 2×OMe), 4.01 (2H, s, CH$_2$) 7.20-7.27 (1H, m, ArH), 7.33-7.37 (1H, m, ArH), 7.46-7.53 (2H, m, 2×ArH). Anal. Calcd. for C$_{16}$H$_{15}$NO$_4$: C, 67.36; H, 5.30; N, 4.91. Found: C, 67.30; H, 5.31; N, 4.85.

Step 2: Synthesis of (2-Hydroxymethyl-3-methyl-8H-3a-aza-cyclopenta[a]inden-1-yl)methanol (DA-1090)

A solution of 3-methyl-8H-3a-azacyclopenta[a]indene-1,2-dicarboxylic acid dimethyl ester (3.14 g, 11 mmol) in anhydrous dichloromethane (30 mL) was added dropwise to a stirred suspension of LiAlH$_4$ (1.04 g, 27.5 mmol) in anhydrous ether (45 mL) at 0° C. The mixture was stirred for 15 min after the addition was complete. The excess LiAlH$_4$ was carefully decomposed by the slow, sequential addition of water (1.3 mL), 15% NaOH aqueous solution (1.3 mL), and water (3.6 mL). The solid inorganic salt was removed by filtration and washed with dichloromethane. The combined filtrate and washings was concentrated in vacuo to dryness. The residue was triturated with ether, the solid product was collected by filtration, and dried to give (2-hydroxymethyl-3-methyl-8H-3a-aza-cyclopenta-[a]inden-1-yl)methanol (DA-1090) 1.95 g (77%): mp 123-125° C.; $^1$H NMR (DMSO-d6) δ 2.53 (3H, s, Me), 3.80 (2H, s, CH$_2$), 4.35 (2H, d, J=5.2 Hz, CH$_2$O), 4.44 (2H, d, J=5.2 Hz, CH$_2$O), 4.47 (1H, t, J=5.2 Hz, exchangeable, OH), 4.61 (1H, t, J=5.2 Hz, exchangeable, OH), 7.07-7.10 (1H, m, Hz, ArH), 7.29-7.33 (1H, m, ArH), 7.46-7.48 (2H, m, 2×ArH). Anal. Calcd. for C$_{14}$H$_{15}$NO$_2$: C, 73.34; H, 6.59; N, 6.11. Found: C, 73.08; H, 6.59; N, 6.04.

Example 2

Synthesis of methyl carbamic acid 3-methyl-2-methylcarbamoyloxymethyl-8H-3a-aza-cyclopenta[a]inden-1-yl methyl ester (DA-1100)

To a solution of DA-1090 (0.80 g, 3.5 mmol) and triethylamine (2.5 mL) in anhydrous dichloromethane (10 mL) was added dropwise methyl isocyanate (2 mL, 35 mmol) in anhydrous dichloromethane (5 mL). The mixture was stirred at room temperature for additional 5 hours. The mixture was concentrated under reduced pressure to dryness. The residue was triturated with a mixture of ether/methanol (15:1), the solid product was collected by filtration, washed with ether (10 mL), and dried in vacuo to yield methyl carbamic acid 3-methyl-2-methylcarbamoyloxymethyl-8H-3a-azacyclopenta[a]inden-1-ylmethyl ester (DA-1100), 1.18 g (98%): mp 86-88° C.; $^1$H NMR (DMSO-d$_6$) δ 2.51 (3H, s, Me), 2.54 and 2.55 (each 3H, d, J=2.0 Hz, 2×N-Me), 3.84 (2H, s, CH$_2$), 4.92 and 4.95 (each 2H, s, 2×CH$_2$), 6.86 (2H, brs, exchangeable, 2×NH), 7.10-7.14 (1H, m, ArH), 7.30-7.34 (1H, m, ArH), 7.47-7.52 (2H, m, 2×ArH). Anal. Calcd. for C$_{18}$H$_{21}$N$_3$O$_4$.H$_2$O: C, 59.82; H, 6.41; N, 11.62. Found: C, 59.30; H, 6.35; N, 11.94.

Example 3

Synthesis of (3-ethyl-2-hydroxymethyl-8H-3a-aza-cyclopenta[a]inden-1-yl)-methanol (DA-1099)

Step 1: Preparation of 1-Propionyl-2,3-dihydro-1H-indole-2-carboxylic acid

To a solution of indoline-2-carboxilic acid (8.16 g, 50 mmol) and triethyl amine (10 mL, 71.74 mmol) in anhydrous CH$_2$Cl$_2$ (60 mL) containing catalytic amount of DMAP was added dropwise a solution of propionyl chloride (5.55 g, 60 mmol) in CH$_2$Cl$_2$ (20 mL) at 0° C. The reaction mixture was stirred at this temperature for 15 min and then at room temperature for 2.5 hours. The reaction mixture was washed successively with 5% aqueous KHSO$_4$ solution (2×20 mL), brine (25 mL), dried over Na$_2$SO$_4$, and evaporated under reduced pressure to dryness. The residue was crystallized from methanol to yield 1-propionyl-2,3-dihydro-1H-indole-2-carboxylic acid as a white solid, 9.19 g (83%): mp 173-175° C.; $^1$H NMR (DMSO-d$_6$) δ1.05 (3H, t, J=7.6 Hz, Me), 2.51 (2H, d, J=7.6 Hz, CH$_2$), 3.17 (1H, d, J=16.0 Hz, CH), 3.57 (1H, dd, J=11.0 Hz, J=16.0 Hz, N—CH), 5.15 (1H, d, J=16.0

Hz, CH), 6.98-7.01 (1H, m, ArH), 7.15-7.23 (2H, m, 2×ArH), 8.07-8.09 (1H, m, ArH), 13.26 (1H, brs, exchangeable, OH). Anal. Calcd. for $C_{12}H_{13}NO_3$: C, 65.74; H, 5.98; N, 6.39. Found: C, 65.73; H, 6.07; N, 6.34.

Step 2: Preparation of 3-Ethyl-8H-3a-azacyclopenta[a]indene-1,2-dicarboxylic acid dimethyl ester A mixture of 1-propionyl-2,3-dihydro-1H-indole-2-carboxylic acid (4.49 g, 20.5 mmol) and dimethyl acetylenedicarboxylate (5.68 g, 40 mmol) in acetic anhydride (40 mL) was stirred in a flask equipped with a reflux condenser and a gas bubbler to monitor carbon dioxide evolution during the reaction. The mixture was heated to 120° C. for 4 hours until no gas was eliminated. The dark solution was concentrated in vacuo to dryness and the solid residue was recrystallized from methanol to yield 3-ethyl-8H-3a-aza-cyclopenta[a]indene-1,2-dicarboxylic acid dimethyl ester, 4.61 g (75%): mp 86-88° C.; $^1$H NMR (DMSO-$d_6$) δ 1.22 (3H, t, J=7.4 Hz, Me), 3.08 (2H, q, J=7.4 Hz, $CH_2$), 3.75 and 3.76 (each 3H, s, 2×OMe), 4.07 (2H, s, $CH_2$), 7.27-7.31 (1H, m, ArH), 7.43-7.47 (1H, m, ArH), 7.59-7.64 (2H, m, ArH). Anal. Calcd. for $C_{17}H_{17}NO_4$: C, 68.21; H, 5.72; N, 4.68. Found: C, 68.22; H, 5.74; N, 4.65.

Step 3: Synthesis of (3-Ethyl-2-hydroxymethyl-8H-3a-azacyclopenta[a]inden-1-yl)methanol (DA-1099)

A solution of 3-ethyl-8H-3a-aza-cyclopenta[a]indene-1,2-dicarboxylic acid dimethyl ester (2.5 g, 8.35 mmol) in anhydrous dichloromethane (30 mL) was added dropwise to a stirred suspension of $LiAlH_4$ (0.793 g, 20.87 mmol) in anhydrous ether (30 mL) at 0° C. The mixture was stirred for 15 min after the addition was completed. The excess hydride was carefully decomposed by the slow, sequential addition of water (1.3 mL), 15% NaOH aqueous solution (1.3 mL), and water (3.6 mL). The solid inorganic salt was filtered and washed with dichloromethane. The combined filtrate and washings was concentrated in vacuo to dryness. The solid residue was triturated with ether, collected the solid product by filtration, and dried in vacuo to yield (3-ethyl-2-hydroxymethyl-8H-3a-azacyclopenta[a]inden-1-yl)-methanol (DA-1099), 1.31 g (64%): mp 131-133° C.; $^1$H NMR (DMSO-$d_6$) δ 1.18 (3H, t, J=7.3 Hz, Me), 2.89 (2H, q, J=7.3 Hz, $CH_2$), 3.81 (2H, s, $CH_2$), 4.36 (2H, d, J=5.2, $CH_2O$), 4.45 (2H, d, J=5.2 Hz, $CH_2O$), 4.47 (1H, t, J=5.2 Hz, exchangeable, OH), 4.63 (1H, t, J=5.2 Hz, exchangeable, OH), 7.06-7.09 (1H, m, ArH), 7.30-7.34 (1H, m, ArH), 7.37-7.39 (1H, m, ArH), 7.45-7.46 (1H, m, ArH). Anal. Calcd for $C_{15}H_{17}NO_2$: C, 74.05; H, 7.04; N, 5.76. Found: C, 73.22; H, 6.94; N, 5.71.

Example 4

Synthesis of methyl carbamic acid 3-ethyl-2-methyl carbamoyloxymethyl-8H-3a-aza-cyclopenta[a]inden-1-ylmethyl ester (DA-1101)

To a solution of (3-ethyl-2-hydroxymethyl-8H-3a-aza-cyclopenta[a]inden-1-yl)-methanol (DA-1099) (0.85 g, 3.5 mmol) and triethylamine (2 mL) in anhydrous dichloromethane (10 mL) was added dropwise a solution of methyl isocyanate (2 mL, 35 mmol) in anhydrous dichloromethane (5 mL). After being stirred at room temperature for 2 hours, the reaction mixture was concentrated in vacuo to dryness. The residue was triturated with a mixture of ether/methanol (15:1), the solid product was collected by filtration, washed with ether, and dried to yield methylcarbamic acid 3-ethyl-2-methyl carbamoyloxymethyl-8H-3a-azacyclopenta[a]inden-1-ylmethyl ester (DA-1101), 1.24 g (99%): mp 165-166° C.; $^1$H NMR (DMSO-$d_6$) δ 1.18 (3H, t, J=7.3 Hz, Me), 2.54 and 2.55 (each 3H, d, J=2.8 Hz, 2×N-Me), 2.93 (2H, q, J=7.3 Hz, $CH_2$), 3.85 (2H, s, $CH_2$), 4.93 and 4.96 (each 2H, s, 2×$CH_2O$), 6.84 and 6.90 (each 1H, brs, exchangeable, 2×NH), 7.11-7.15 (1H, m, ArH), 7.33-7.37 (1H, m, ArH), 7.42-7.45 (1H, m, ArH), 7.48-7.50 (1H, m, ArH). Anal. Calcd. for $C_{19}H_{23}N_3O_4.H_2O$: C, 60.78; H, 6.71; N, 11.19. Found: C, 63.57; H, 6.71; N, 11.71.

Example 5

Synthesis of (2-hydroxymethyl-3-phenyl-8H-3a-azacyclopenta[a]inden-1-yl)-methanol (DA-1011)

Step 1: Preparation of 1-Benzoyl-2,3-dihydro-1H-indole-2-carboxylic acid

To a solution of indoline-2-carboxilic acid (6.52 g, 40 mmol) and triethyl amine (11 mL, 78 mmol) in anhydrous $CH_2Cl_2$ (100 mL) was added dropwise a solution of benzoyl chloride (5.62 g, 40 mmol) in $CH_2Cl_2$ (25 mL) at 0° C. The reaction mixture was stirred at this temperature for 15 min and then at room temperature for additional 2.5 hours. The reaction mixture was washed successively with 5% aqueous $KHSO_4$ solution (2×20 mL), brine (25 mL), dried over $Na_2SO_4$, and evaporated under reduced pressure to dryness. The residue was chromatographed on a silica gel column (3×35 cm) using $CHCl_3$/MeOH (100:1) as the eluent. The main fractions containing the desired product was combined, evaporated under reduced pressure to dryness and the solid residue was recrystallized from MeOH to give the known 1-benzoyl-2,3-dihydro-1H-indole-2-carboxylic acid, 10.66 g (81%): mp 209-210° C. (191-193° C.)[19]; $^1$H NMR (DMSO-$d_6$) δ 3.09 (1H, d, J=16.3 Hz, CH), 3.61-3.63 (1H, m, N—CH), 4.97 (1H, brs, CH), 7.06 (1H, m, ArH), 7.25-7.26 (2H, m, 2×ArH), 7.49 (5H, m, 5×ArH), 8.14-8.17 (1H, m, ArH), 13.01 (1H, brs, exchangeable, OH). MS: m/z 268.0 $(M+H)^+$.

Step 2: Preparation of 3-Phenyl-8H-3a-azacyclopenta[a]indene-1,2-dicarboxylic acid dimethyl ester A mixture of 1-benzoyl-2,3-dihydro-1H-indole-2-carboxylic acid (7.48 g, 28 mmol) and dimethyl acetylenedicarboxylate (4.55 g, 32 mmol) in acetic anhydride (40 mL) was heated for 4.5 h at 120° C. until no gas was eliminated. The dark solution was concentrated in vacuo to dryness and the solid residue was recrystallized from methanol to yield 3-phenyl-8H-3a-azacyclopenta[a]indene-1,2-dicarboxylic acid dimethyl ester, 7.5 g (77%): mp 149-151° C.; $^1$H NMR (DMSO-$d_6$) δ 3.62 (3H, s, OMe), 3.79 (3H, s, OMe), 4.15 (2H, s, $CH_2$), 6.60-6.67 (1H, m, ArH), 7.18-7.23 (2H, m, 2×ArH), 7.51-7.67 (6H, m, 6×ArH). Anal. Calcd for $C_{21}H_{17}NO_4$: C, 69.40; H, 5.21; N, 3.85. Found: C, 69.42; H, 4.65; N, 3.83.

Step 3: Synthesis of (2-Hydroxymethyl-3-phenyl-8H-3a-azacyclopenta[a]inden-1-yl-methanol (DA-1011)

A solution of 3-phenyl-8H-3a-aza-cyclopenta[a]indene-1,2-dicarboxylic acid dimethyl ester (2.08 g, 6 mmol) in anhydrous dichloromethane (35 mL) was added dropwise to a stirred suspension of $LiAlH_4$ (0.568 g, 15 mmol) in anhydrous ether (50 mL) at 0° C. The mixture was stirred for 15 min after the addition was completed. The excess hydride was carefully decomposed by the slow, sequential addition of water (2 mL), 15% NaOH aqueous solution (2 mL), and water (4 mL). The solid inorganic salt was filtered and washed with dichloromethane. The combined filtrate and washings was concentrated in vacuo to dryness. The residue was triturated with ether, the solid product was collected by filtration, and dried to yield (2-hydroxymethyl-3-phenyl-8H-3a-azacyclopenta[a]inden-1-yl)methanol (DA-1011), 1.24 g (71%): mp 169-171° C.; $^1$H NMR (DMSO-d$_6$) δ3.93 (2H, s, CH$_2$), 4.27 and 4.55 (each 2H, d, J=4.8 Hz, 2×CH$_2$), 4.68 and 4.80 (each 1H, t, J=4.8 Hz, exchangeable, 2×OH), 6.73-6.74 (1H, m, ArH), 7.03-7.05 (1H, m, ArH), 7.09-7.12 (1H, m, ArH), 7.44-7.55 (6H, m, 6×ArH). Anal. Calcd. for C$_{19}$H$_{17}$NO$_2$.0.3H$_2$O: C, 76.90; H, 5.98; N, 4.72. Found: C, 76.89; H, 6.02; N, 4.56.

Example 6

Synthesis of Methylcarbamic acid 2-methylcarbamoyloxymethyl-3-phenyl-8H-3a-aza-cyclopenta[a]inden-1-ylmethylester (DA-1022)

To a solution of (2-hydroxymethyl-3-phenyl-8H-3a-azacyclopenta[a]inden-1-yl) methanol (DA-1011) (0.73 g, 2.5 mmol) and triethylamine (2.5 mL) in anhydrous dichloromethane (12 mL) was added dropwise a solution of methyl isocyanate (1.47 mL, 25 mmol) in anhydrous dichloromethane (5 mL). After being stirred at room temperature for 2 hours, the mixture was concentrated in vacuo to dryness. The residue was triturated with a mixture of ether/methanol (15:1), the solid product was collected by filtration, washed with ether (5 mL), and dried to afford methylcarbamic acid 2-methylcarbamoyl-oxymethyl-3-phenyl-8H-3a-azacyclopenta[a]inden-1-ylmethyl ester (DA-1022), 0.87 g (86%); mp 196-198° C.; $^1$H NMR (CDCl$_3$) δ 2.78 and 2.80 (each 3H, d, J=4.7 Hz, 2×N-Me), 3.94 (2H, s, CH$_2$), 4.69 and 4.73 (each 1H, brs, exchangeable, 2×NH), 5.01 and 5.20 (each 2H, s, 2×CH$_2$O), 6.76-6.77 (1H, m, ArH), 7.02-7.05 (2H, m, 2×ArH), 7.36-7.38 (1H, m, ArH), 7.42-7.48 (5H, m, 5×ArH). Anal. Calcd. for C$_{23}$H$_{23}$N$_3$O$_4$: C, 68.13; H, 5.72; N, 10.36. Found: C, 67.69; H, 5.75; N, 10.31.

Example 7

Synthesis of (2-hydroxymethyl-6-methoxy-3-(4'-methoxyphenyl)-8H-3a-aza-cyclopenta[a]inden-1-yl)methanol (DA-1130)

Step 1: Preparation of 5-Methoxy-1-(4'-methoxybenzoyl)-1H-indole-2-carboxylic acid To a solution of commercially available 5-methoxyindole-2-carboxylic acid (6.69 g, 35 mmol) and triethylamine (10 mL, 71.7 mmol) in anhydrous CH$_2$Cl$_2$ (70 mL) containing catalytic amount of DMAP was added dropwise a solution of 4-methoxybenzoyl chloride (6.20 g, 36.34 mmol) in CH$_2$Cl$_2$ (15 mL) at 0° C. The reaction mixture was stirred at this temperature for 15 min and then at room temperature for 4 hours. The reaction mixture was washed successively with 5% aqueous KHSO$_4$ solution (2×20 mL), brine (25 mL), dried over Na$_2$SO$_4$, and evaporated under reduced pressure to dryness. The solid residue was recrystallized from methanol to yield 5-methoxy-1-(4'-methoxybenzoyl)-1H-indole-2-carboxylic acid as a white solid (7.4 g, 65%): mp 185-187° C.; $^1$H NMR (DMSO-d$_6$) δ 3.80 and 3.85 (each 3H, s, 2×OMe), 7.02 (1H, dd, J=2.5 Hz and J=9.0 Hz, ArH), 7.07 (2H, d, J=8.9 Hz, 2×ArH), 7.28 (1H, d, J=2.5 Hz, ArH), 7.33 (1H, s, ArH), 7.38 (1H, d, J=9.0 Hz, ArH), 7.59 (2H, d, J=8.9 Hz, 2×ArH), 13.2 (1H, brs, exchangeable, OH). Anal. Calcd. for C$_{18}$H$_{15}$NO$_5$.0.1H$_2$O: C, 65.73; H, 4.65; N, 4.25. Found: C, 65.77; H, 4.61; N, 4.24.

Step 2: Preparation of 5-Methoxy-1-(4'-methoxybenzoyl)-2,3-dihydro-1H-indole-2-carboxylic acid To a solution of 5-methoxy-1-(4'-methoxybenzoyl)-1H-indole-2-carboxylic acid (7.02 g, 21.57 mmol) in ethanol (200 mL) was added platinum oxide (0.7 g). The mixture was hydrogenated for 6 hours at 32 psi. The reaction mixture was filtered through a pad of Celite. The filter cake was washed with ethanol. The combined filtrate and washings was evaporated in vacuo to dryness. The solid residue was recrystallized from ethanol to yield 5-methoxy-1-(4'-methoxybenzoyl)-2,3-dihydro-1H-indole-2-carboxylic acid, 6.35 g (90%): mp 151-152° C.; $^1$H NMR (DMSO-d$_6$) δ 3.05 (1H, m, CH), 3.56-3.63 (1H, m, N—CH), 3.70 (3H, s, OMe), 3.81 (3H, s, OMe), 4.97-5.01 (1H, m, CH), 6.67 (1H, br, ArH), 6.86 (2H, m, 2×ArH), 7.00 (2H, d, J=8.6 Hz, 2×H), 7.45 (2H, J=8.6 Hz, 2×ArH), 12.92 (1H, brs, exchangeable, OH). Anal. Calcd. for C$_{18}$H$_{17}$NO$_5$.0.1H$_2$O: C, 65.69; H, 5.26; N, 4.25. Found: C, 65.61; H, 5.48; N, 4.17.

Step 3: Preparation of 6-methoxy-3-(4-methoxyphenyl)-8H-3a-aza-cyclopenta[a]indene-1,2-dicarboxylic acid dimethyl ester A mixture of 5-methoxy-1-(4'-methoxybenzoyl)-2,3-dihydro-1H-indole-2-carboxylic acid (4.24 g, 12.9 mmol) and dimethyl acetylenedicarboxylate (2.4 mL, 19.5 mmol) in acetic anhydride (24 mL) was heated for 4.5 hours at 120° C. until no gas eliminated. The dark solution was concentrated in vacuo to dryness and the solid residue was recrystallized from methanol to yield 6-methoxy-3-(4-methoxy-phenyl)-8H-3a-azacyclopenta[a]indene-1,2-dicarboxylic acid dimethyl ester, 3.75 g (71%): mp 240-242° C.; $^1$H NMR (DMSO-d6) δ 3.60 (3H, s, COOMe), 3.73 and 3.77 (each 3H, s, 2×OMe), 3.85 (3H, s, COOMe), 4.09 (2H, s, CH$_2$), 6.55 (1H, d, J=8.8 Hz, ArH), 6.77 (1H, dd, J=2.6 Hz and J=8.8 Hz, ArH), 7.08 (2H, d, J=8.7 Hz, 2×ArH), 7.19 (1H, d, J=2.4 Hz, ArH), 7.42 (2H, d, J=8.7 Hz, 2×ArH). Anal. Calcd. for C$_{23}$H$_{21}$NO$_5$: C, 67.84; H, 5.20; N, 3.44. Found: C, 67.83; H, 5.19; N, 3.39.

Step 4: Synthesis of (2-Hydroxymethyl-6-methoxy-3-(4-methoxyphenyl)-8H-3a-aza-cyclopenta-[a]inden-1-yl)methanol (DA-1130)

A solution of 6-methoxy-3-(4-methoxyphenyl)-8H-3a-aza-cyclopenta[a]indene-1,2-dicarboxylic acid dimethyl ester (1.73 g, 3.56 mmol) in anhydrous dichloromethane (20 mL) was added dropwise to a stirred suspension of LiAlH$_4$ (0.45 g, 11.85 mmol) in anhydrous ether (40 mL) at 0° C. The mixture was stirred for 15 min after the addition was completed. The excess hydride was carefully decomposed by the slow, sequential addition of water (1 mL), 15% NaOH aqueous solution (1 mL), and water (3 mL). The solid inorganic salt was removed by filtration and washed with dichloromethane. The combined filtrate and washings was concentrated in vacuo to dryness. The solid product was suspended in ether, collected by filtration, and dried to yield (2-hydroxymethyl-6-methoxy-3-(4-methoxyphenyl)-8H-3a-azacyclopenta[a]inden-1-yl)methanol (DA-1130), 1.35 g (91%): mp 186-187° C.; $^1$H NMR (DMSO-d$_6$) δ 3.71 and 3.84 (each 3H, s, 2×OMe), 3.87 (2H, s, CH$_2$), 4.24 and 4.53 (each 2H, d, J=4.4 Hz, 2×CH$_2$O), 4.56 and 4.71 (each 1H, t, J=4.4 Hz, exchangeable, 2×OH), 6.64 (1H, d, J=8.7 Hz, ArH), 6.69 (1H, dd, J=2.5 Hz and J=8.7 Hz, ArH), 7.07 (2H, d, J=8.7 Hz, 2×ArH), 7.10 (1H, d, J=2.3 Hz, ArH), 7.40 (2H, d, J=8.7 Hz, 2×ArH). Anal. Calcd. for C$_{21}$H$_{21}$NO$_4$.1.3H$_2$O: C, 67.29; H, 6.29; N, 3.74. Found: C, 67.19; H, 5.90; N, 3.58.

Example 8

Synthesis of methylcarbamic acid 6-methoxy-3-(4-methoxyphenyl)-2-methylcarbamoyl-oxymethyl-8H-3a-aza-cyclopenta[a]inden-1-ylmethyl ester (DA-1131)

To a solution of (2-hydroxymethyl-6-methoxy-3-(4-methoxyphenyl)-8H-3a-aza-cyclopenta[a]-inden-1-yl)methanol (DA-1130) (0.954 g, 2.71 mmol) and triethylamine (1.5 mL) in anhydrous dichloromethane (10 mL) was added dropwise a solution of methyl isocyanate (0.95 mL, 16.24 mmol) in anhydrous dichloromethane (5 mL). After being stirred at room temperature for additional 5 hours. The mixture was concentrated in vacuo to dryness. The solid residue was triturated with a mixture of ether/methanol (15:1), collected by filtration, and dried to yield methylcarbamic acid 6-methoxy-3-(4-methoxyphenyl)-2-methylcarbamoyloxymethyl-8H-3a-azacyclopenta[a]inden-1-ylmethyl ester (DA-1131), 1.17 g (93%): mp 110-112° C.; $^1$H NMR (DMSO-$d_6$) δ 2.55 and 2.58 (each 3H, d, J=4.5 Hz, 2×Me), 3.71 and 3.84 (each 3H, s, 2×OMe), 3.92 (2H, s, $CH_2$), 4.80 and 5.02 (each 2H, s, 2×$CH_2$O), 6.60 (1H, d, J=8.7 Hz, ArH), 6.71 (1H, dd, J=2.5 Hz and J=8.7 Hz, 2×ArH), 6.88-6.92 (2H, brs, exchangeable, 2×NH), 7.08 (2H, d, J=8.6 Hz m, 2×ArH), 7.13 (1H, d, J=2.5 Hz, ArH), 7.38 (2H, d, J=8.6 Hz, 2×ArH). Anal. Calcd. for $C_{25}H_{27}N_3O_6$: C, 64.50; H, 5.85; N, 9.03. Found: C, 63.41; H, 5.80; N, 8.84.

By following the same synthetic route, compounds of Formula I (DA-1099, 1024, 1011, 1003, 1025, 1005, 1123, 1097, 1126, and 1128, see Table 1) and Formula II (DA-1101, 1026, 1022, 1004, 1027, 1012, 1124, 1125, 1127, and 1129, see Table 2) were synthesized. The yields of physical data of these agents are shown in Tables 1-2.

TABLE 1

The yields and melting points (mp) of (2-hydroxymethyl-8H-3a-aza-cyclopenta[a]inden-1-yl)methanol derivatives (Exemplary compounds of Formula I)

Formula 1 (A)

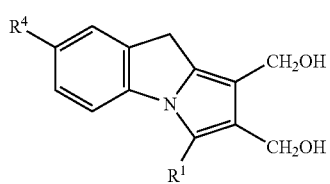

| Compd. | Formula | $R^4$ | $R^1$ | Yield (%) | mp (° C.) |
|---|---|---|---|---|---|
| DA-1090 | $C_{14}H_{15}NO_2$ | H | Me | 77 | 123-125 |
| DA-1099 | $C_{15}H_{17}NO_2$ | H | Et | 64 | 131-133 |
| DA-1011 | $C_{19}H_{17}NO_2 \cdot 0.3H_2O$ | H | $C_6H_5$ | 71 | 169-171 |
| DA-1024 | $C_{19}H_{16}FNO_2$ | H | 4'-$FC_6H_4$ | 72 | 164-166 |
| DA-1003 | $C_{19}H_{16}ClNO_2$ | H | 4'-$ClC_6H_4$ | 71 | 213-215 |
| DA-1025 | $C_{19}H_{15}F_2NO_2$ | H | 3',4'-$diFC_6H_3$ | 69 | 146-147 |
| DA-1005 | $C_{20}H_{19}NO_3 \cdot 0.67H_2O$ | H | 4'-$MeOC_6H_4$ | 79 | 143-144 |
| DA-1123 | $C_{20}H_{19}NO_3$ | H | 2'-$MeOC_6H_4$ | 76 | 132-134 |
| DA-1097 | $C_{21}H_{21}NO_4$ | H | 3',4'-$diMeOC_6H_3$ | 77 | 160-162 |
| DA-1126 | $C_{21}H_{21}NO_4$ | H | 2',6'-$diMeOC_6H_4$ | 70 | 171-173 |
| DA-1128 | $C_{22}H_{23}NO_5$ | H | 3',4',5'-$triMeOC_6H_2$ | 75 | 132-134 |
| DA-1130 | $C_{21}H_{21}NO_4$ | MeO | 4'-$MeOC_6H_4$ | 91 | 186-187 |

TABLE 2

The yields and melting points (mp) of methylcarbamic acid 2-methyl-carbamoyloxymethyl-8H-3a-aza-cyclopenta[a]inden-1-ylmethylester derivatives (Exemplary compounds of Formula II)

Formula II (A)

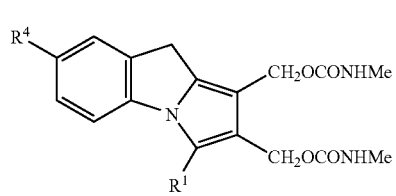

| Compd. | Formula | $R^4$ | $R^1$ | Yield (%) | mp (° C.) |
|---|---|---|---|---|---|
| DA-1100 | $C_{18}H_{21}N_3O_4 \cdot H_2O$ | H | Me | 98 | 86-88 |
| DA-1101 | $C_{19}H_{23}N_3O_4 \cdot H_2O$ | H | Et | 99 | 165-166 |
| DA-1022 | $C_{23}H_{23}N_3O_4$ | H | $C_6H_5$ | 86 | 196-198 |
| DA-1026 | $C_{23}H_{22}FN_3O_4$ | H | 4'-$FC_6H_4$ | 87 | 199-200 |
| DA-1004 | $C_{23}H_{22}ClN_3O_4$ | H | 4'-$ClC_6H_4$ | 96 | 204-206 |
| DA-1027 | $C_{23}H_{21}F_2N_3O_4 \cdot 0.5H_2O$ | H | 3',4'-$diFC_6H_3$ | 85 | 151-152 |
| DA-1012 | $C_{24}H_{25}N_3O_5 \cdot 0.5H_2O$ | H | 4'-$MeOC_6H_4$ | 70 | 152-153 |
| DA-1124 | $C_{24}H_{25}N_3O_5$ | H | 2'-$MeOC_6H_4$ | 87 | 200-203 |

TABLE 2-continued

The yields and melting points (mp) of methylcarbamic acid 2-methyl-carbamoyloxymethyl-8H-3a-aza-cyclopenta[a]inden-1-ylmethylester derivatives (Exemplary compounds of Formula II)

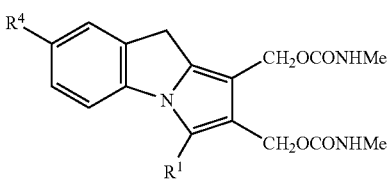

Formula II (A)

| Compd. | Formula | $R^4$ | $R^1$ | Yield (%) | mp (° C.) |
|---|---|---|---|---|---|
| DA-1125 | $C_{25}H_{27}N_3O_6$ | H | 3',4'-diMeOC$_6$H$_3$ | 91 | 165-168 |
| DA-1127 | $C_{25}H_{27}N_3O_6$ | H | 2',6'-diMeOC$_6$H$_4$ | 90 | 154-156 |
| DA-1129 | $C_{26}H_{29}N_3O_7$ | H | 3',4',5'-triMeOC$_6$H$_2$ | 95 | 204-206 |
| DA-1131 | $C_{25}H_{27}N_3O_6$ | MeO | 4'-MeOC$_6$H$_4$ | 93 | 110-112 |

Example 9

Synthesis of (2-Hydroxymethyl-3-methyl-5,10-dihydropyrrolo[1,2-b]isoquinolin-1-yl)methanol (DA-1107) and methylcarbamic acid 3-methyl-1-methylcarbamoyloxymethyl-5,10-dihydro-pyrrolo[1,2-b]isoquinolin-2-ylmethyl ester (DA-1108)

Step 1: Preparation of 3-carboxy-1,2,3,4-tetrahydroquinoline

A suspension of D,L-phenylalanine (50 g, 0.303 mol) in con. HCl (325 mL) and 37% formaldehyde (110 mL) was heated to a gentle reflux with vigorous stirring for 30 min. Additional formaldehyde (50 ml) and con. HCl (110 mL) was added and continuously heated for 4 hours. The reaction mixture was cooled to room temperature and the solid product was collected by filtration, washed with methanol (30 mL), and dried to give the known 3-carboxy-1,2,3,4-tetrahydroquinoline, 64.09 g (98.9%): mp 295-298° C. (>326° C., dec.) (Julian P L, J. Chem. Soc. 1948, 70, 180-183) as an enantiomeric mixture; $^1$H NMR (DMSO-d$_6$) δ 3.10-3.18 (1H, m, CH), 3.28-3.34 (1H, m, CH), 4.27 (2H, s, CH$_2$), 4.39 (1H, m, CH), 7.25-7.27 (4H, m, 4×ArH), 9.89 (1H, brs, exchangeable, NH); 10.06 (1H, brs, exchangeable, OH); MS: m/z 177.0 (M+H)$^+$.

Step 2: Preparation of 2-Acetyl-1,2,3,4-tetrahydroisoquinoline-3-carboxylic acid To a mixture of acetone (75 mL) and 2N NaOH (100 mL) was added portionwise 1,2,3,4-tetrahydro-isoquinoline-3-carboxylic acid hydrochloride (10.00 g, 46.8 mmol). After stirring for 10 min, acetyl chloride (7.38 g, 94 mmol) in acetone (50 mL) was added slowly into the above solution, followed with 2N NaOH at room temperature. The reaction mixture was maintained at a pH>10 and stirred for 1 hour. The acetone was evaporated in vacuo and acidified the residue by adding 3N HCl. The separated solid was collected by filtration, washed several times with water, and dried to afford the known 2-acetyl-1,2,3,4-tetrahydroisoquinoline-3-carboxylic acid as an enantiomeric mixture, 7.90 g, (76.9%); mp 178-180° C. (170-171° C.):[21] $^1$H NMR (DMSO-d$_6$) δ 2.15 (3H, s, Me), 3.02-3.24 (2H, m), 4.29-4.75 (2H, m), 4.98-5.17 (1H, m), 7.17-7.21 (4H, m, 4×ArH), 12.70 (1H, brs, exchangeable, OH); m/z219.0 (M+H)$^+$.

Step 3: Preparation of 3-Methyl-5,10-dihydro-pyrrolo[1,2-b]isoquinoline-1,2-dicarboxylic acid dimethyl ester A mixture of 2-acetyl-1,2,3,4-tetrahydroisoquinoline-3-carboxylic acid (3.00 g, 13.6 mmol) and dimethyl acetylenedicarboxylate (2.84 g, 20 mmol) in acetic anhydride (25 mL) was heated at 65-70° C. for 1.5 hours. The reaction mixture was then cooled and evaporated under reduced pressure to dryness. The residue was recrystallized from methanol to give 3-methyl-5,10-dihydropyrrolo[1,2-b]-isoquinoline-1,2-dicarboxylic acid dimethyl ester, 3.29 g, (80.2%); mp 152-154° C.; $^1$H NMR (DMSO-d$_6$) δ 2.40 (3H, s, Me), 3.70 (3H, s, COOMe), 3.72 (3H, s, COOMe), 4.18 (2H, s, CH$_2$), 5.06 (2H, s, CH$_2$), 7.29-7.32 (2H, m, 2×ArH), 7.35-7.39 (2H, m, 2×ArH); m/z 299.0 (M+H)$^+$. Anal. Calcld. for $C_{17}H_{17}NO_4$: C, 68.22; H, 5.72; N, 4.68. Found: C, 68.29; H, 5.77; N, 4.67.

Step 4: Synthesis of (2-Hydroxymethyl-3-methyl-5,10-dihydropyrrolo[1,2-b]isoquinolin-1-yl)methanol (DA-1107)

A solution of 3-methyl-5,10-dihydropyrrolo[1,2-b]-isoquinoline-1,2-dicarboxylic acid dimethyl ester (2.39 g, 8 mmol) in anhydrous dichloromethane (20 mL) was added dropwise into a stirred suspension of LiAlH$_4$ (0.69 g, 18.4 mmol) in anhydrous diethyl ether (30 mL) at 10-15° C. The reaction mixture was further stirred for 2 hours after the addition was completed. The mixture was cooled in an ice bath and the excess hydride was destroyed by the sequential addition of water (1.2 mL), 15% aqueous NaOH (1.2 mL), and water (3.6 mL) at 0° C. The mixture was filtered, and the inorganic solid was removed by filtration, washed with hot THF (300 mL). The combined filtrate and washings was evaporated in vacuo to dryness. The solid residue was recrystallized from dichloromethane/ether to give (2-hydroxymethyl-3-methyl-5,10-dihydropyrrolo[1,2-b]isoquinolin-1-yl)methanol (DA-1107), 1.47 g (76.2%); mp 99-101° C.; $^1$H NMR (DMSO-d$_6$) δ 2.22 (3H, s, Me), 3.96 (2H, s, CH$_2$), 4.34 and 4.39 (each 3H, brs, CH$_2$ and exchangeable, OH), 4.93 (2H, s, CH$_2$), 7.26 and 7.34 (each 2H, brs, 4×ArH); m/z 243.0 (M+H)$^+$ Anal. Calcld. for $C_{15}H_{17}NO_2$.0.1H$_2$O): C, 73.50; H, 7.07; N, 5.71. Found: C, 73.42; H, 6.97; N, 5.71.

Example 10

Synthesis of methylcarbamic acid 3-methyl-1-methylcarbamoyloxymethyl-5,10-dihydro-pyrrolo[1,2-b]isoquinolin-2-ylmethyl ester (DA-1108)

To a mixture of (2-hydroxymethyl-3-methyl-5,10-dihydropyrrolo[1,2-b]isoquinolin-1-yl)methanol (DA-1107, 0.80 g, 3.2 mmol) and triethylamine (1.01 g, 10 mmol) was added dropwise a solution of methylisocyanate (1.14 g, 20 mmol) in anhydrous dichloromethane (8 mL). After being stirred at ambient temperature for 16 hours under an argon atmosphere, the reaction mixture was evaporated in vacuo to dryness. The solid residue was recrystallized from dichloromethane/hexane to give methylcarbamic acid 3-methyl-1-methylcarbamoyl-oxymethyl-5,10-dihydropyrrolo[1,2-b]isoquinolin-2-ylmethyl ester (DA-1108), 0.53 g (44.5%); mp 174-176° C.; $^1$H NMR (DMSO-$d_6$) δ 2.23 (3H, s, Me), 2.51 and 2.52 (each 3H, s, 2×Me), 3.99 (2H, s, $CH_2$), 4.88, 4.92, and 4.95 (each 2H, s, 3×$CH_2$), 6.74 (2H, brs, exchangeable, 2×NH), 7.21-7.32 (2H, m, 2×ArH), 7.34-7.38 (2H, m, 2×ArH); m/z 356.1 (M+H)$^+$ Anal. Calcld. for $C_{19}H_{23}N_3O_4$: C, 63.85; H, 6.49; N, 11.76. Found: C, 63.79; H, 6.47; N, 11.74.

Example 11

Synthesis of [3-(4-chlorophenyl)-2-hydroxymethyl-5,10-dihydropyrrolo[1,2-b]-isoquinolin-1-yl]methanol (DA-1116)

Step 1: Preparation of 2-(4-Chlorobenzoyl)-1,2,3,4-tetrahydro-isoquinoline-3-carboxylic acid 1,2,3,4-Tetrahydroisoquinoline-3-carboxylic acid hydrochloride (10.00 g, 46.8 mmol) was added portionwise into a mixture of acetone (75 mL) and 2N NaOH (75 mL). To this solution was added dropwise acetyl chloride (8.75 mL, 50 mmol) in acetone (50 mL) followed with 2N NaOH at room temperature. The reaction mixture was maintained at a pH>10 and stirred for 1 hour. The acetone was removed by evaporation under reduced pressure and acidified the residue by adding 3N HCl. The separated solid was collected by filtration, washed several times with water, and dried to give 2-(4-chlorobenzoyl)-1,2,3,4-tetrahydroisoquinoline-3-carboxylic acid as an enantiomeric mixture, 13.80 g (93.4%); mp 77-79° C.; $^1$H NMR (DMSO-$d_6$) δ 2.92 (1H, dd, J=5.9 Hz and J=15.8 Hz, CH), 3.29 (1H, d, J=15.8 Hz, CH), 4.12 (1H, d, J=5.9 Hz, CH), 4.49 and 5.02 (each 1H, d, J=17.4 Hz, $CH_2$), 7.09-7.17 (4H, m, 4×ArH), 7.40-7.58 (4H, m, 4×ArH); m/z 315.00 (M+H)$^+$ Anal. Calcld. for $C_{17}H_{14}ClNO_3$: C, 64.67; H, 4.47; N, 4.44. Found: C, 64.65; H, 4.46; N, 4.41.

Step 2: Preparation of 3-(4-Chlorophenyl)-5,10-dihydropyrrolo[1,2-b]isoquinoline-1,2-dicarboxylic acid dimethyl ester A mixture of 2-acetyl-1,2,3,4-tetrahydroisoquinoline-3-carboxylic acid (9.47 g, 30 mmol) and dimethyl acetylenedicarboxylate (4.55 g, 32 mmol) in acetic anhydride (60 mL) was heated at 60-70° C. for 15 min. The reaction mixture was then cooled and evaporated in vacuo to dryness. The solid residue was recrystallized from ethanol to give 3-(4-chlorophenyl)-5,10-dihydropyrrolo[1,2-b]-isoquinoline-1,2-dicarboxylic acid dimethyl ester, 10.41 g (87.7%); mp 164-166° C.; $^1$H NMR (DMSO-$d_6$) δ 3.60 (3H, s, COOMe), 3.76 (3H, s, COOMe), 4.32 (2H, s, $CH_2$), 4.98 (2H, s, $CH_2$), 7.20-7.26 (1H, m, ArH), 7.27-7.33 (2H, m, 2×ArH), 7.39-7.43 (1H, m, ArH), 7.48 (2H, d, J=8.5 Hz, ArH), 7.57 (2H, d, J=8.5 Hz, ArH); m/z 395.00 (M+H)$^+$ Anal. Calcld. for $C_{22}H_{18}ClNO_4$: C, 66.75; H, 4.58; N, 3.54. Found: C, 66.71; H, 4.55; N, 3.52.

Step 3: Synthesis of [3-(4-Chlorophenyl)-2-hydroxymethyl-5,10-dihydropyrrolo[1,2-b]isoquinolin-1-yl]methanol (DA-1116)

A solution of the 3-(4-chlorophenyl)-5,10-dihydropyrrolo[1,2-b]isoquinoline-1,2-dicarboxylic acid dimethyl ester (5.03 g, 15 mmol) in anhydrous dichloromethane (120 mL) was added dropwise into a stirred suspension of $LiAlH_4$ (1.31 g, 34.5 mmol) in anhydrous diethyl ether (50 mL) at 10-15° C. The reaction mixture was further stirred for 2 hours after the addition was completed. The mixture was cooled in an ice bath and the excess hydride was destroyed by the sequential addition of water (2.0 mL), 15% aqueous NaOH (2.0 mL), and water (6.0 mL). The mixture was filtered to remove inorganic salt, the solid residue was washed with hot THF (300 mL). The combined filtrate and washings was evaporated in vacuo to dryness and the solid residue was recrystallized from dichloromethane/ether to give [3-(4-chlorophenyl)-2-hydroxymethyl-5,10-dihydro-pyrrolo[1,2-b]isoquinolin-1-yl]methanol (DA-1116), 3.12 g (61.4%); mp 170-171° C.; $^1$H NMR (DMSO-$d_6$) δ 4.06 (2H, s, $CH_2$), 4.28 (2H, d, J=5.1 Hz, $CH_2$), 4.50 (2H, d, J=5.1 Hz, $CH_2$), 4.55 (1H, t, J=5.1 Hz, exchangeable, OH), 4.57 (1H, t, J=5.1 Hz, exchangeable, OH), 4.98 (2H, s, $CH_2$), 7.18-7.20 (1H, m, ArH), 7.25-7.30 (2H, m, ArH), 7.36-7.40 (1H, m, ArH), 7.49 (2H, d, J=8.5 Hz, 2×ArH), 7.54 (2H, d, J=8.5 Hz, 2×ArH); m/z 339.82 (M+H)$^+$ Anal. Calcld. for $C_{20}H_{18}ClNO_2$: C, 70.69; H, 5.34; N, 4.12. Found: C, 70.42; H, 5.29; N, 4.19.

Example 12

Synthesis of methylcarbamic acid 3-(4-chlorphenyl)-2-methylcarbamoyloxymethyl-5,10-dihydropyrrolo [1,2-b]isoquinolin-1-ylmethyl ester (DA-1117)

To a mixture of [3-(4-chlorophenyl)-2-hydroxymethyl-5,10-dihydropyrrolo[1,2-b]isoquinolin-1-yl]methanol (DA-1116, 1.02 g, 3.0 mmol) and triethylamine (1.45 g, 14.3 mmol) in anhydrous dichloromethane (15 mL) was added a solution of methylisocyanate (0.856 g, 15 mmol) in anhydrous dichloromethane (5 mL). After being stirred at room temperature for 6 hours, the mixture was concentrated in vacuo to dryness. The solid residue was recrystallized from methanol/ether to give, methylcarbamic acid 3-(4-chlorophenyl)-2-methylcarbamoyloxymethyl-5,10-dihydropyrrolo[1,2-b]-isoquinolin-1-ylmethyl ester (DA-1117), 1.11 g (81.9%); mp 194-196° C.; $^1$H NMR (DMSO-$d_6$) 2.54 (3H, d, J=5.1 Hz, Me), 2.55 (3H, d, J=5.1 Hz, Me), 4.09 (2H, s, $CH_2$), 4.80 (2H, s, $CH_2$), 4.97 (2H, s, $CH_2$), 5.03 (2H, s, $CH_2$), 6.81 (2H, brs, exchangeable, 2×NH), 7.17-7.23 (1H, m, ArH), 7.24-7.30 (2H, m, 2×ArH), 7.36-7.40 (1H, m, ArH), 7.46 (2H, d, J=8.2 Hz, 2×ArH), 7.56 (2H, d, J=8.2 Hz, 2×ArH); m/z 453.93 (M+H)$^+$ Anal. Calcld. for $C_{24}H_{24}ClN_3O_4$: C, 63.50; H, 5.33; N, 9.26. Found: C, 63.41; H, 5.28; N, 9.18.

Example 13

Synthesis of [3-(3,4-difluorophenyl)-2-hydroxymethyl-5,10-dihydropyrrolo-[1,2-b]isoquinolin-1-yl] methanol (DA-1112)

Step 1: Preparation of 4-Difluorobenzoyl)-1,2,3,4-tetrahydro-isoquinoline-3-carboxylic acid 1,2,3,4-Tetrahydroisoquinoline-3-carboxylic acid hydrochloride (10.0 g, 46.8 mmol) was added portionwise into a mixture of acetone (75 mL) and 2N NaOH (50 mL). To this solution was added dropwise acetyl chloride (10.23 mL, 58 mmol). The reaction mixture was maintained at a pH>10 and stirred for 1 hour. The acetone was removed by evaporation under reduced pressure and the remaining solution was acidified by adding 3N HCl. The separated solid was collected by filtration, washed several times with water, and dried to give 2-(3,4-difluorobenzoyl)-1,2,3,4-tetrahydroisoquinoline-3-carboxylic acid as an enantiomeric mixture, 14.67 g, (98.8%);

mp 89-91° C.; $^1$H NMR (DMSO-d$_6$) δ 2.93 (1H, dd, J=6.0 Hz, J=15.6 Hz, CH), 3.31 (1H, d, J=15.6 Hz, CH), 4.14 (1H, d, J=6.0 Hz, CH), 4.48 and 5.03 (each 1H, d, J=17.5 Hz, CH$_2$), 7.09-7.15 (5H, m, 5×ArH), 7.44-7.58 (2H, m, 2×ArH); m/z 317.00 (M+H)$^+$ Anal. Calcld. for C$_{17}$H$_{13}$F$_2$NO$_3$: C, 64.35; H, 4.13; N, 4.41. Found: C, 64.29; H, 4.09; N, 4.35.

Step 2: Preparation of 3-(3,4-Difluorophenyl)-5,10-dihydropyrrolo[1,2-b]isoquinoline-1,2-dicarboxylic acid dimethyl ester A mixture of 2-(3,4-difluorobenzoyl)-1,2,3,4-tetrahydroisoquinoline-3-carboxylic acid (11.10 g, 35 mmol) and dimethyl acetylenedicarboxylate (7.39 g, 52 mmol) in acetic anhydride (70 mL) was heated at 60-70° C. for 15 min. The reaction mixture was then cooled and evaporated in vacuo to dryness. The solid residue was recrystallized from ethanol to give 3-(3,4-difluorophenyl)-5,10-dihydropyrrolo[1,2-b]isoquinoline-1,2-dicarboxylic acid dimethyl ester 10.97 g, (78.6%); mp 142-144° C.; $^1$H NMR (DMSO-d$_6$) δ 3.61 (3H, s, Me), 3.77 (3H, s, Me), 4.31 (2H, s, CH$_2$), 5.00 (2H, s, CH$_2$), 7.21-7.27 (1H, m, ArH), 7.29-7.35 (3H, m, 3×ArH), 7.37-7.43 (1H, m, ArH), 7.50-7.65 (2H, m, 2×ArH); m/z 397.00 (M+H)$^+$ Anal. Calcld. for C$_{22}$H$_{17}$F$_2$NO$_4$: C, 66.50; H, 4.31; N, 3.52. Found: C, 66.65; H, 4.51; N, 3.47.

Step 3: Synthesis of [3-(3,4-Difluorophenyl)-2-hydroxymethyl-5,10-dihydropyrrolo[1,2-b]isoquinolin-1-yl]methanol (DA-1112)

A solution of the 3-(3,4-difluorophenyl)-5,10-dihydropyrrolo[1,2-b]isoquinoline-1,2-dicarboxylic acid dimethyl ester (7.94 g, 20 mmol) in anhydrous dichloromethane (180 mL) was added dropwise into a stirred suspension of LiAlH$_4$ (1.75 g, 46 mmol) in anhydrous diethyl ether (50 mL) at 10-15° C. The reaction mixture was further stirred for 2 hours after the addition was completed. The mixture was cooled in an ice bath and the excess hydride was destroyed by the sequential addition of water (2.5 mL), 15% aqueous NaOH (2.5 mL), and water (9.0 mL) at 0° C. The reaction mixture was filtered and the solid residue was washed with hot THF (300 mL). The combined filtrate and washings was evaporated to dryness in vacuo to dryness and the solid residue was recrystallized from dichloromethane/ether to give [3-(3,4-difluorophenyl)-2-hydroxymethyl-5,10-dihydropyrrolo[1,2-b]isoquinolin-1-yl]methanol (DA-1112), 4.57 g (67%); mp 145-146° C.; $^1$H NMR (DMSO-d$_6$) δ 4.06 (2H, s, CH$_2$), 4.28 (2H, d, J=5.1 Hz, CH$_2$), 4.50 (2H, d, J=5.1 Hz, CH$_2$), 4.55 (1H, t, J=5.1 Hz, exchangeable, OH), 4.62 (1H, t, J=5.1 Hz, exchangeable, OH), 5.02 (2H, s, CH$_2$), 7.17-7.22 (1H, m, ArH), 7.24-7.35 (3H, m, 3×ArH), 7.34-7.36 (1H, m, ArH), 7.50-7.58 (2H, m, ArH) m/z 341.00 (M+H)$^+$ Anal. Calcld. for C$_{20}$H$_{17}$F$_2$NO$_2$: C, 70.37; H, 5.02; N, 4.10. Found: C, 70.31; H, 4.91; N, 4.19.

Example 14

Synthesis of methylcarbamic acid 3-(3,4-difluorophenyl)-2-methylcarbamoyloxymethyl-5,10-dihydropyrrolo[1,2-b]isoquinolin-1-methyl ester (DA-1113)

To a mixture of [3-(3,4-difluorophenyl)-2-hydroxymethyl-5,10-dihydropyrrolo[1,2-b]isoquinolin-1-yl]methanol (DA-1112, 1.00 g, 2.9 mmol) and triethylamine (1.08 g, 10.7 mmol) in anhydrous dichloromethane (10 mL) was added dropwise a solution of methylisocyanate (0.855 g, 15 mmol) in anhydrous dichloromethane (5 mL). After being stirred at room temperature for 3 hours, the mixture was evaporated in vacuo to dryness. The solid residue was recrystallized from MeOH/ether to give methylcarbamic acid 3-(3,4-difluorophenyl)-2-methylcarbamoyloxymethyl-5,10-dihydropyrrolo[1,2-b]isoquinolin-1-methyl ester (DA-1113), 1.02 g (76.6%); mp 190-192° C.; $^1$H NMR (DMSO-d$_6$) δ 2.54 and 2.55 (each 3H, d, J=4.7 Hz, 2×Me), 4.09 (2H, s, CH$_2$), 4.81 (2H, s, CH$_2$), 4.99 (2H, s, CH$_2$), 5.03 (2H, s, CH$_2$), 6.83 (2H, brs, exchangeable 2×NH), 7.19-7.23 (1H, m, ArH), 7.26-7.31 (3H, m, 3×ArH), 7.37-7.39 (1H, m, ArH), 7.53-7.60 (2H, m, 2×ArH); m/z 454.00 (M+H)$^+$ Anal. Calcld. for C$_{24}$H$_{23}$F$_2$N$_3$O$_4$: C, 63.29; H, 5.09; N, 9.23. Found: C, 63.27; H, 5.01; N, 9.20.

Example 15

Synthesis of [2-hydroxymethyl-3-(4-methoxyphenyl)-5,10-dihydropyrrolo[1,2-b]-isoquinolin-1-yl]-methanol (DA-1106) and methylcarbamic acid 3-(4-methoxyphenyl)-2-methylcarbamoyloxymethyl-5,10-dihydropyrrolo[1,2-b]isoquinolin-1-ylmethyl ester (DA-1109)

Step 1: Preparation of 2-(4-Methoxybenzoyl)-1,2,3,4-tetrahydroisoquinoline-3-carboxylic acid 1,2,3,4-Tetrahydroisoquinoline-3-carboxylic acid hydrochloride (10.0 g, 46.8 mmol) was added portionwise into a solution of acetone (75 mL) and 2N NaOH (50 mL). To this solution was then added dropwise acetyl chloride (9.38 g, 55 mmol) in acetone (50 mL) and followed with 2N NaOH at room temperature. The solution was maintained at a pH>10 and stirred for 2 hours. The acetone was evaporated in vacuo and the remaining solution was made acidic with 3N HCl. The separated solid was collected by filtration, washed several times with water, and dried to give 2-(4-methoxybenzoyl)-1,2,3,4-tetrahydroisoquinoline-3-carboxylic acid as an enatiomeric mixture, 10.37 g (72%); mp 178-180° C.; $^1$H NMR (CDCl$_3$) δ 3.10-3.14 (2H, m, CH$_2$), 3.85 (3H, s, OMe), 4.62 (2H, m, 2×CH), 5.39 (1H, m, CH), 6.89-6.95 (3H, m, 3×ArH), 7.20 (3H, m, 3×ArH), 7.45 (2H, m, 2×ArH); m/z 311.0 (M+H)$^+$ Anal. Calcld. for (C$_{18}$H$_{17}$NO$_4$. 0.2H$_2$O): C, 68.64; H, 5.57; N, 4.44. Found: C, 68.63; H, 5.62; N, 4.27.

Step 2: Preparation of 3-Methyl-5,10-dihydro-pyrrolo[1,2-b]isoquinoline-1,2-dicarboxylic acid dimethyl ester A mixture of 2-acetyl-1,2,3,4-tetrahydroisoquinoline-3-carboxylic acid (6.22 g, 20 mmol) and dimethyl acetylenedicarboxylate (4.26 g, 30 mmol) in acetic anhydride (50 mL) was heated at 60-70° C. for 3.5 hours. The reaction mixture was then cooled to room temperature and then evaporated under reduced pressure to dryness. The solid residue was recrystallized from ethanol to give 3-methyl-5,10-dihydropyrrolo[1,2-b]isoquinoline-1,2-dicarboxylic acid dimethyl ester 7.38 g, (94.4%); mp 155-158° C.; $^1$H NMR (DMSO-d$_6$) δ δ 3.70 (3H, s, OMe), 3.86 (3H, s, COOMe), 3.89 (3H, s, COOMe), 4.41 (2H, s, CH$_2$), 4.86 (2H, s, CH$_2$), 7.01 (2H, d, J=8.5 Hz, ArH), 7.12 (1H, m, ArH), 7.22-7.25 (1H, m, ArH), 7.30-7.32 (1H, m, ArH), 7.37 (2H, d, J=8.5 Hz, ArH), 7.37-7.38 (1H, m, ArH); m/z 391.0 (M+H)$^+$ Anal. Calcld. for C$_{23}$H$_{21}$NO$_5$. 0.1H$_2$O: C, 70.25; H, 5.43; N, 3.56. Found: C, 70.15; H, 5.44; N, 3.49.

Step 3: Synthesis of [2-Hydroxymethyl-3-(4-methoxyphenyl)-5,10-dihydropyrrolo[1,2-b]isoquinolin-1-yl]methanol (DA-1106)

A solution of the 3-(4-methoxyphenyl)-5,10-dihydropyrrolo[1,2-b]isoquinoline-1,2-dicarboxylic acid dimethyl ester (3.91 g, 10 mmol) in anhydrous dichloromethane (20 mL) was added dropwise to a stirred suspension of $LiAlH_4$ (0.87 g, 23 mmol) in anhydrous diethyl ether (30 mL) at 10-15° C. The reaction mixture was further stirred for 2 hours after the addition was completed. The mixture was cooled in an ice bath and the excess hydride was destroyed by the sequential addition of water (1.2 mL), 15% aqueous NaOH (1.2 mL), and water (3.6 mL) at 0° C. The inorganic salt was removed by filtration, was washed with hot THF (300 mL), and the combined filtrate and washings was evaporated under reduced pressure to dryness. The solid residue was recrystallized from dichloromethane/ether to give [2-hydroxymethyl-3-(4-methoxyphenyl)-5,10-dihydropyrrolo[1,2-b]-isoquinolin-1-yl]methanol (DA-1106), 2.29 g (68.4%); mp 174-176° C.; $^1H$ NMR (DMSO-$d_6$) δ 3.82 (3H, s, OMe), 4.05 (2H, s, $CH_2$), 4.26 (2H, d, J=5.0 Hz, $CH_2$), 4.45-4.54 (4H, m, $CH_2$ and exchangeable, 2×OH), 4.93 (2H, s, $CH_2$), 7.05 (2H, d, J=8.4 Hz, ArH), 7.17-7.21 (1H, m, ArH), 7.25-7.28 (2H, m, ArH), 7.38 (2H, d, J=8.4 Hz, ArH), 7.37-7.39 (1H, m, ArH); m/z 451.9 $(M+H)^+$ Anal. Calcld. for $C_{21}H_{21}NO_3$ $0.2H_2O$: C, 74.40; H, 6.36; N, 4.13. Found: C, 74.41; H, 6.30; N, 4.13.

Example 16

Synthesis of methylcarbamic acid 3-(4-methoxyphenyl)-2-methylcarbamoyloxymethyl-5,10-dihydropyrrolo[1,2-b]isoquinolin-1-ylmethyl ester (DA-1109)

To a mixture of [2-hydroxymethyl-3-(4-methoxy-phenyl)-5,10-dihydropyrrolo[1,2-b]isoquinolin-1-yl]-methanol (DA-1106, 1.00 g, 2.9 mmol) and triethylamine (1.45 g, 14.3 mmol) in anhydrous dichloromethane (10 mL) was added dropwise a solution of methylisocyanate (1.65 g, 29 mmol) in anhydrous dichloromethane (5 mL). After being stirred at room temperature for 6 hours, the reaction mixture was evaporated in vacuo to dryness. The solid residue was recrystallized from dichloromethane/hexane to give methylcarbamic acid 3-(4-methoxyphenyl)-2-methylcarbamoyloxymethyl-5,10-dihydropyrrolo[1,2-b]isoquinolin-1-ylmethyl ester (DA-1109), 1.17 g (87%); mp 182-184° C.; $^1H$ NMR (DMSO-$d_6$) δ 2.54 and 2.55 (each 3H, d, J=4.8 Hz, 2×Me), 3.85 (3H, s, Me), 4.08 (2H, s, $CH_2$), 4.78 (2H, s, $CH_2$), 4.93 (2H, s, $CH_2$), 5.02 (2H, s, $CH_2$), 6.81 (2H, brs, exchangeable, 2×NH), 7.06 (2H, d, J=8.6 Hz, ArH), 7.18-7.22 (1H, m, ArH), 7.27-7.29 (2H, m, 2×ArH), 7.35 (2H, d, J=8.6 Hz, ArH), 7.35-7.39 (1H, m, ArH); m/z 311.00 $(M+H)^+$ Anal. Calcld. For $C_{25}H_{27}N_3O_5$: C, 66.80; H, 6.05; N, 9.35. Found: C, 66.72; H, 6.01; N, 9.31.

Therefore, compounds of Formula III (DA-1107, 1116, 1112, 1 and 1106, see Table 3) and Formula IV (DA-1108, 1117, 1113, and 1109, see Table 4) were synthesized. The yields of physical data of these agents are shown in Tables 3-4.

TABLE 3

The yields and melting points (mp) of (1-hydroxymethyl-5,10-dihydropyrrolo[1,2-b]isoquinolin-2-yl)methanol derivatives (Exemplary compounds of Formula III)

Formula III (A)

| Compd. | Formula | $R^1$ | Yield (%) | mp (° C.) |
|---|---|---|---|---|
| DA-1107 | $C_{15}H_{17}NO_2$ | Me | 76.2 | 99-101 |
| DA-1116 | $C_{20}H_{18}ClNO_2$ | 4'-$ClC_6H_4$ | 61.4 | 170-171 |
| DA-1112 | $C_{20}H_{17}F_2NO_2$ | 3',4'-$diFC_6H_3$ | 67 | 145-146 |
| DA-1106 | $C_{21}H_{21}NO_3$ $0.2 H_2O$ | 4'-$MeOC_6H_4$ | 68.4 | 174-176 |

TABLE 4

The yields and melting points (mp) of methylcarbamic acid 2-methylcarbamoyloxymethyl-5,10-dihydropyrrolo[1,2-b]isoquinolin-1-methyl ester derivatives (Exemplary compounds of Formula IV)

Formula IV (A)

| Compd. | Formula | $R^1$ | Yield (%) | mp (° C.) |
|---|---|---|---|---|
| DA-1108 | $C_{19}H_{23}N_3O_4$ | Me | 44.5 | 174-176 |
| DA-1117 | $C_{24}H_{24}ClN_3O_4$ | 4'$ClC_6H_4$ | 81.9 | 194-196 |
| DA-1113 | $C_{24}H_{23}F_2N_3O_4$ | 3',4'-$diFC_6H_3$ | 76.6 | 190-192 |
| DA-1109 | $(C_{25}H_{27}N_3O_5)$ | 4'-$MeOC_6H_4$ | 87 | 182-184 |

Example 17

In Vitro Cytotoxicity Studies

Human colon carcinoma HCT-116 cells, human prostate adenocarcinoma PC-3 and adenocarcinoma SK-OV-3 cells were obtained from American Type Culture Collection (ATCC, Rockville, Md.). Human mammary carcinoma (MX-1) tumor cells were obtained from MSKCC cell bank. The CCRF-CEM human lymphoblastic leukemia cells and their vinblastine resistant subline (CCRF-CEM/VBL, 680-fold resistance in vitro) were obtained from Dr. William Beck of the University of Illinois, Chicago, and CCRF-CEM/Taxol (330-fold resistance in vitro). Resistant cells CCRF-CEM/taxol were produced by exposing the parent cells to increasing sublethal concentration ($IC_{50}$-$IC_{90}$) of paclitaxel for six months.

Cytotoxicity Assays

In preparation for in vitro cytotoxicity assays, cells were cultured at an initial density 2-5×$10^4$ cells per milliliter. They were maintained in a 5% $CO_2$-humidified atmosphere at 37° C. in RPMI medium 1640 (GIBCO/BRL) containing penicillin (100 units/mL), streptomycin (100 μg/mL, GIBCO/BRL), and 5% heat-inactivated FBS. For cells grown in suspension (such as CCRF-CEM and its sublines), cytotoxicity was measured, by using XTT microculture method in 96-well microtiter plates (Scudiero D A et al., Cancer Res. 1988, 48, 4827-4833). For solid tumor cells growing in a monolayer (such as MX-1 and HCT-116), cytotoxicity of the drug was determined, in duplicate, in 96-well microtiter plates by using the sulforhodamine B method (Skehan P et al., *J. Natl. Cancer Inst* 1990, 82, 1107-1112). For both methods, the absorbance of each well was measured with a microplate reader (Power Wave XS, Bio-Tek, Winooski, Vt.) after 72-hr incubation as described previously (Chou T-C et al., *Proc. Natl. Acad. Sci. USA* 2001, 98, 8113-8118). Dose-effect relationship data from 6 to 7 concentrations of each drug, in duplicate, were analyzed by using a computer program (Chou T-C et al., ComboSyn, Inc., Paramus, N J. 2005) based on the median-effect principle and plot (Chou T-C et al., *Adv. Enzyme Regul.* 1984, 22, 27-55; Chou T-C, *Pharmacol. Rev.* 2006, 58, 621-681).

Table 5 shows the potency of the compounds disclosed herein in inhibiting tumor cell growth in vitro. The $IC_{50}$ is defined by the concentration required to inhibit tumor cell growth by 50%. It demonstrated that these agents exhibited potent cytotoxicity against human lymphoblastic leukemia (CCRF/CEM) as well as the solid tumors (mammary MX-1 and colon HCT-116) cell growth in vitro with submicromolar or micromolar $IC_{50}$ values. The growth inhibition of the compounds disclosed herein against human lymphoblastic leukemic cells (CCRF-CEM) and its drug-resistant sublines (resistant to vinblastine and taxol, CCRF-CEM/VBL and CCRF-CEM/taxol, respectively) is also shown in Table 5. The results indicated that these compounds have little or no cross-resistance to either Taxol or Vinblastine. It suggested that the compounds disclosed herein were neither a good substrate for membrane multidrug transporters of p-glycoprotein nor mutated tubulin. Thus, the compounds disclosed herein are effective against multiple drug resistant tumors.

TABLE 5

Potency of representative cyclopenta[a]indenes against CCRF-CEM leukemic sublines, MX-1 and HCT-116 solid tumor cell growth in vitro

| | $IC_{50}$ (μM)[a] | | | | |
|---|---|---|---|---|---|
| Compd | CCRF/CEM | CCRF-CEM/VBL[b] | CCRF-CEM/Taxol[b] | MX-1 | HCT-116 |
| 1,2-Bis(methanol) derivatives of cyclopenta[a]indenes (Exemplary compounds of Formula I) | | | | | |
| DA-1090 | 0.076 | 0.0297 [0.39x][c] | 0.0663 [0.87x] | 0.357 | 0.332 |
| DA-1099 | 0.356 | 0.133 [0.37x] | 0.229 [0.64x] | 1.075 | 0.825 |
| DA-1011 | 0.252 | 0.213 [0.85x] | 0.224 [0.89x] | 1.351 | 1.851 |
| DA-1024 | 4.25 | 4.07 [0.96x] | 11.0 [2.6x] | 22.279 | 8.067 |
| DA-1003 | 4.27 | 2.53 [0.59x] | 4.22 [1.00x] | 6.126 | 5.592 |
| DA-1025 | 4.91 | 7.27 [1.98x] | 7.78 [1.6x] | 7.003 | 10.773 |
| DA-1005 | 1.16 | 1.67 [1.4x] | 1.66 [1.4x] | 10.818 | 5.832 |
| DA-1123 | 1.007 | 1.903 [1.89x] | 2.677 [2.68x] | 8.643 | 13.358 |
| DA-1097 | 1.042 | 1.143 [1.1x] | 1.949 [1.87x] | 11.078 | 4.088 |
| DA-1126 | 8.144 | 0.251 [0.03x] | 0.741 [0.09x] | 25.488 | 43.682 |
| DA-1128 | 2.052 | 1.143 [0.56x] | 1.035 [0.50x] | 17.644 | 30.564 |
| DA-1130 | 0.118 | 0.061 [0.52x] | 0.13 [1.10x] | 1.517 | 0.61 |
| 1,2-Bis(methylcarbamate) derivatives of cyclopenta[a]indenes (Exemplary compounds of Formula II) | | | | | |
| DA-1100 | 0.188 | 0.126 [0.67x] | 0.067 [0.36x] | 0.355 | 0.297 |
| DA-1101 | 0.068 | 0.078 [1.15x] | 0.099 [1.46x] | 0.670 | 0.707 |
| DA-1022 | 0.357 | 1.62 [4.5x] | 0.556 [1.6x] | 5.918 | 0.761 |
| DA-1026 | 0.137 | 0.307 [2.2x] | 0.284 [2.1x] | 0.744 | 0.397 |
| DA-1004 | 5.90 | 3.19 [0.54x] | 2.34 [0.40x] | 10.144 | 9.480 |
| DA-1027 | 0.639 | 0.632 [0.99x] | 0.644 [1.0x] | 7.842 | 0.878 |
| DA-1012 | 0.049 | 0.070 [1.4x] | 0.058 [1.2x] | 1.940 | 2.745 |
| DA-1124 | 0.136 | 0.243 [1.79x] | 0.360 [2.65x] | 1.327 | 0.151 |
| DA-1125 | 0.350 | 0.374 [1.07x] | 0.497 [1.42x] | 1.838 | 0.680 |
| DA-1127 | 0.64 | 0.697 [1.08x] | 0.616 [0.96x] | 5.482 | 1.11 |
| DA-1129 | 11.8 | 8.401 [0.71x] | 14.27 [1.21x] | 7.25 | 1.83 |
| DA-1131 | 0.062 | 0.0639 [1.03x] | 0.0962 [1.55x] | 0.878 | 0.455 |
| 1,2-Bis(methanol) derivatives of 5,10-dihydrpyrrolo[1,2-b]isoquinoline (Exemplary compounds of Formula III) | | | | | |
| DA-1107 | 0.081 | 0.093 [1.15x] | 0.098 [1.21x] | 0.616 | 0.281 |
| DA-1116 | 0.60 | 0.543 [0.91x] | 0.601 [1.00x] | 3.271 | 2.635 |
| DA-1112 | 1.135 | 1.007 [0.89x] | 0.745 [0.66x] | 6.673 | 2.915 |
| DA-1106 | 0.228 | 0.111 [0.49x] | 0.232 [1.02x] | 1.941 | 1.03 |

TABLE 5-continued

Potency of representative cyclopenta[a]indenes against CCRF-CEM leukemic sublines, MX-1 and HCT-116 solid tumor cell growth in vitro

| Compd | CCRF/CEM | CCRF-CEM/VBL[b] | CCRF-CEM/Taxol[b] | MX-1 | HCT-116 |
|---|---|---|---|---|---|
| 1,2-Bis(carbamate) derivatives of 5,10-dihydrpyrrolo[1,2-b]isoquinoline (Exemplary compounds of Formula IV) | | | | | |
| DA-1108 | 0.128 | 0.076 [0.59x] | 0.111 [0.87x] | 1.683 | 1.157 |
| DA-1117 | 0.191 | 0.208 [1.09x] | 0.216 [1.13x] | 1.173 | 0.356 |
| DA-1113 | 0.488 | 0.519 [1.06x] | 0.643 [1.32x] | 2.708 | 0.358 |
| DA-1109 | 0.184 | 0.111 [0.60x] | 0.161 [0.88x] | 1.307 | 1.111 |
| Taxol | 0.0013 | 0.429 [330x] | 1.274 [980x] | 0.035 | 0.0013 |
| Vinblastine | 0.00073 | 0.078 [106.2x] | 0.496 [679.5x] | 0.0029 | 0.0018 |

[a]Cell growth inhibition was measured by the XTT assay for leukemic cells and the SRB assay for solid tumor cells after 72-hr incubation using a microplate spectrophotometer as described previously (Chou T-C et al., Proc. Natl. Acad. Sci. USA 2001, 98, 8113-8118). Similar in vitro results were obtained by using the Cell Counting Kit-8 for the CCK-8 assays as described by technical manual of Dojindo Molecular Technologies, Inc. (Gaithersburg, MD). $IC_{50}$ values were determined from dose-effect relationship at six or seven concentrations of each drug by using the CompuSyn software by Chou and Martin (Chou T-C et al., ComboSyn, Inc., Paramus, NJ. 2005) based on the median-effect principle and plot. Ranges given for Taxol and Vinblastine were mean ± SE (n = 4).
[b]CCRF-CEM/Taxol and CCRF-CEM/VBL are subcell lines of CCRF-CEM cells that are 330-fold resistant to Taxol, and 680-fold resistant to Vinblastine, respectively, when comparing with the $IC_{50}$ of the parent cell line.
[c]Numbers in the brackets are fold of cross-resistant determined by comparison with the corresponding $IC_{50}$ of the parent cell line.

Example 18

In Vivo Studies

Athymic nude mice bearing the nu/nu gene were obtained from NCI, Frederick, Md. and used for all human tumor xenografts. Male nude mice, 6 weeks or older, weighing 20-24 g or more were used. Compounds were administered via the tail vein for i.v. injection or infusion as described previously (Chou T-C et al., Proc. Natl. Acad. Sci. USA 2001, 98, 8113-8118). Various formulations were prepared for injections into the mice for chemotherapeutic studies. As an example, a drug was dissolved in DSMO to make a 25 mg/ml fresh solution, 0.4 ml of this solution was mixed with 0.3 ml of Tween 80, plus 1.3 ml to make 2 ml of 5 mg/ml solution. Bolus injection volume was 0.1-0.2 ml per mouse.

Figure 2A:
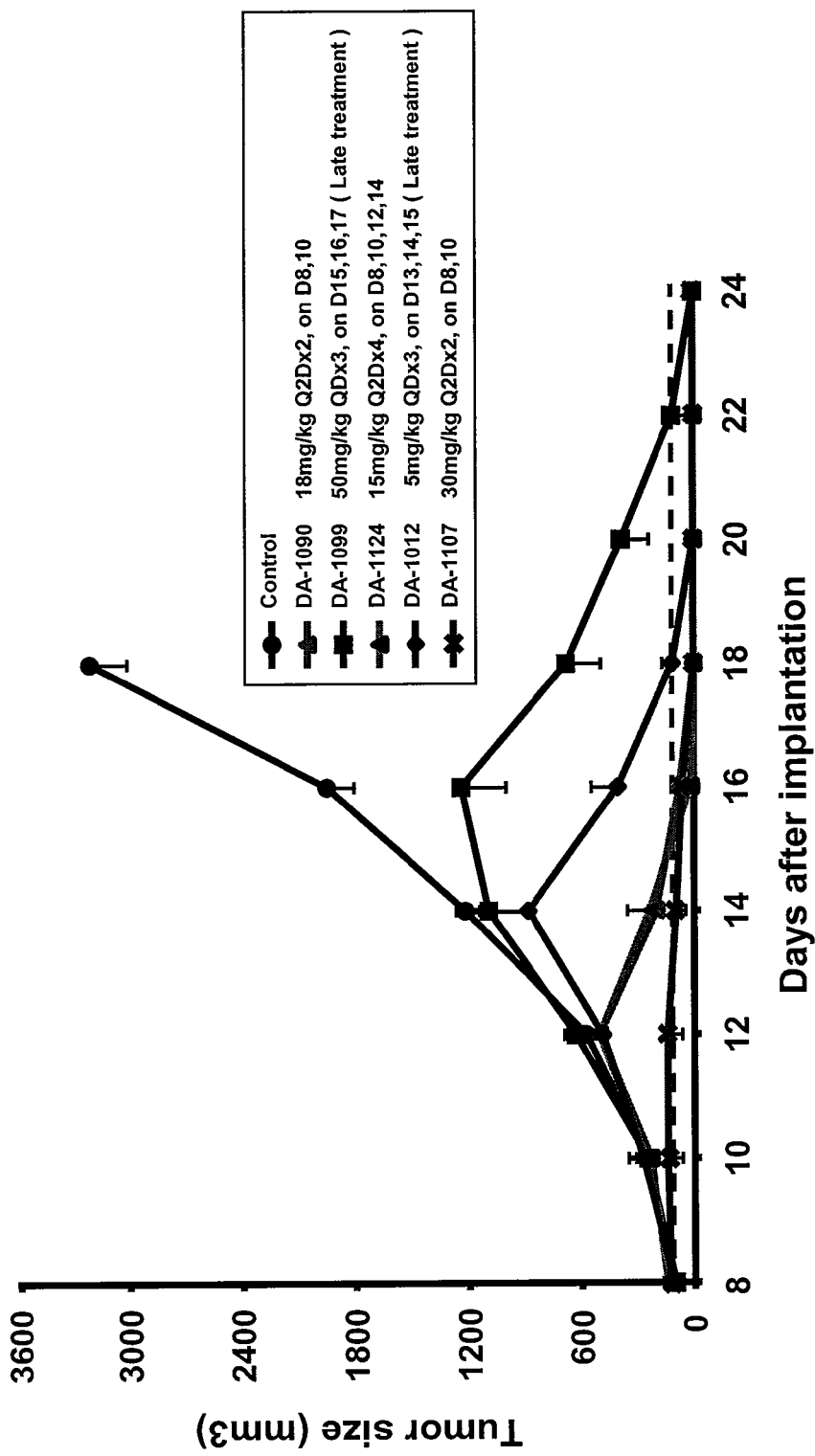
FIGS. 2A-B illustrates the therapeutic effect of DA-1090, 1099, 1124, 1012 and 1107 in nude mice bearing human mammary carcinoma MX-1 xenograft (i.v. inj, n=3-4), average tumor size changes (FIG. 2A) and average body weight changes (FIG. 2B).
Figure 2B:
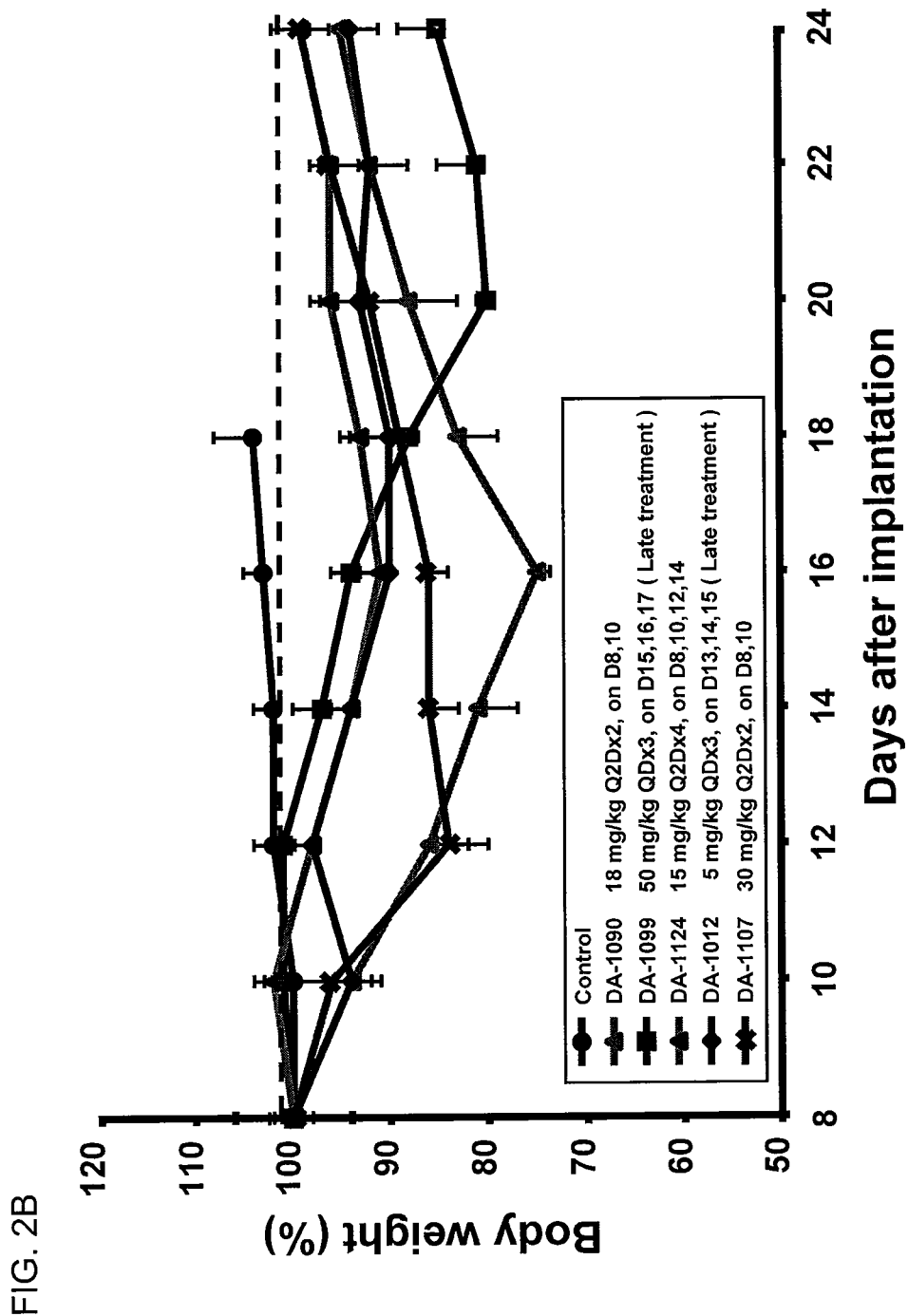

Athymic nude mice bearing the nu/nu gene were used for human breast tumor MX-1 xenograft (FIGS. 2, 2A and 2B). Nude mice were obtained from National Cancer Institute, Frederick, Md. Male mice, 6 weeks old or older, weighing 22 g or more were used for experiments with subcutaneous tumor inoculation as described previously (Chou T-C, Pharmacol. Rev. 2006, 58, 621-681). Drug was administrated via the tail vein by iv injection. Tumor volumes were assessed by measuring length×width×height (or width) by using caliper. An example of vehicle used was 20 µL DMSO in 180 µL saline. All animal studies were conducted in accordance with the guidelines of the U.S. National Institutes of Health Guide for the Care and Use of Animals and the protocol approved by the Institutional Animal Care and Use Committee.

FIG. 2 shows the in vivo antitumor therapeutic effect of the exemplary compounds disclosed herein. Nude mice bearing human tumor were treated with these agents at the dose of 5-30 mg/kg, daily (QD) 3 times, for DA-1099/18 mg/kg, and DA-1012/5 mg/kg or every other two days (Q2D), two times, for DA-1090/18 mg/kg, DA-1124/15 mg/kg, and DA-1107/30 mg/kg, via intravenous injection, resulted in tumor total disappearance (or complete remission, CR) with low toxicity.

Figure 3A:
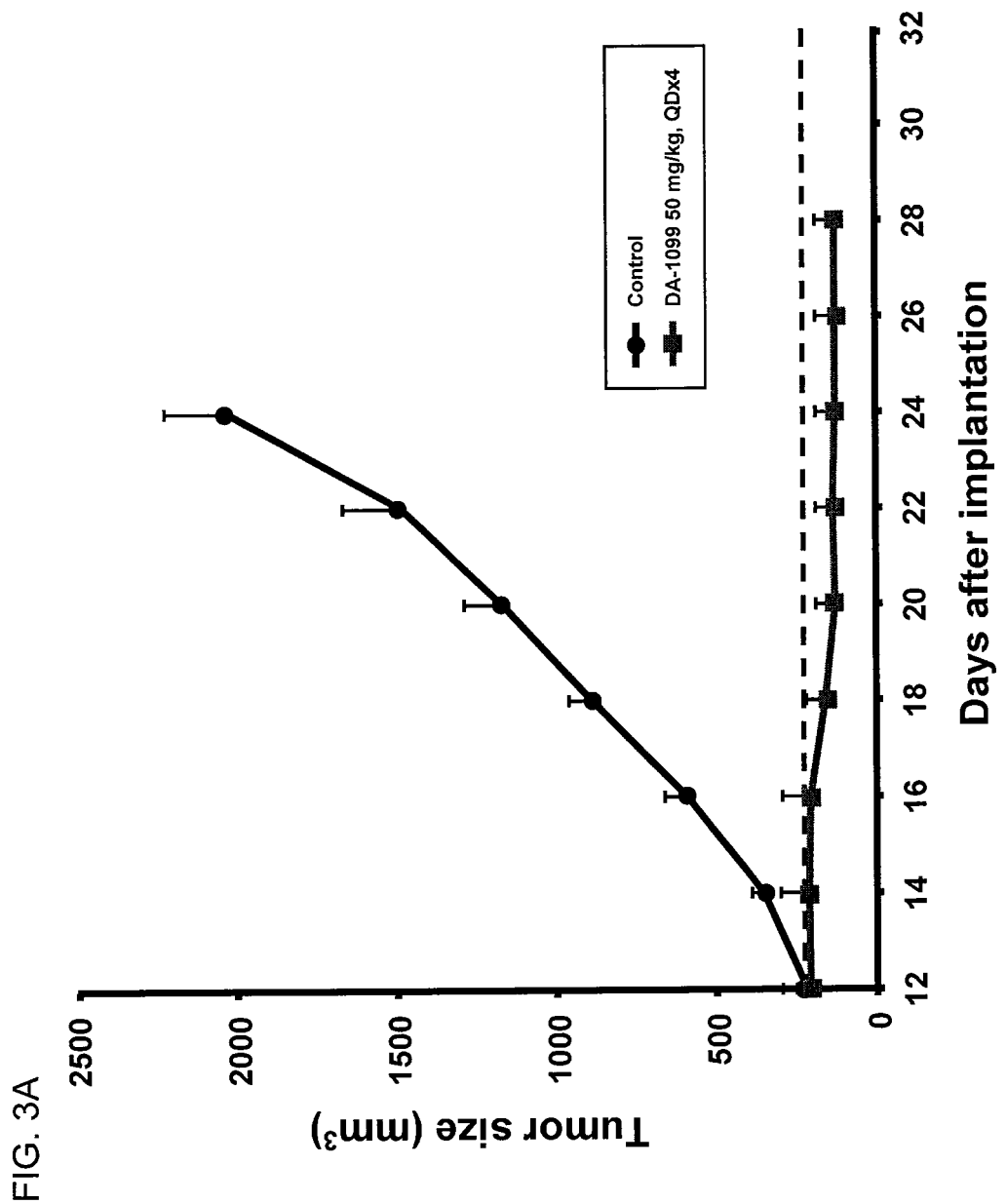
FIGS. 3A-B illustrates the therapeutic effect of DA-1099 in nude mice bearing human prostate adenocarcinoma PC-3 xenograft (i.v. inj., n=3), average tumor size changes (FIG. 3A) and average body weight changes (FIG. 3B).
Figure 3B:
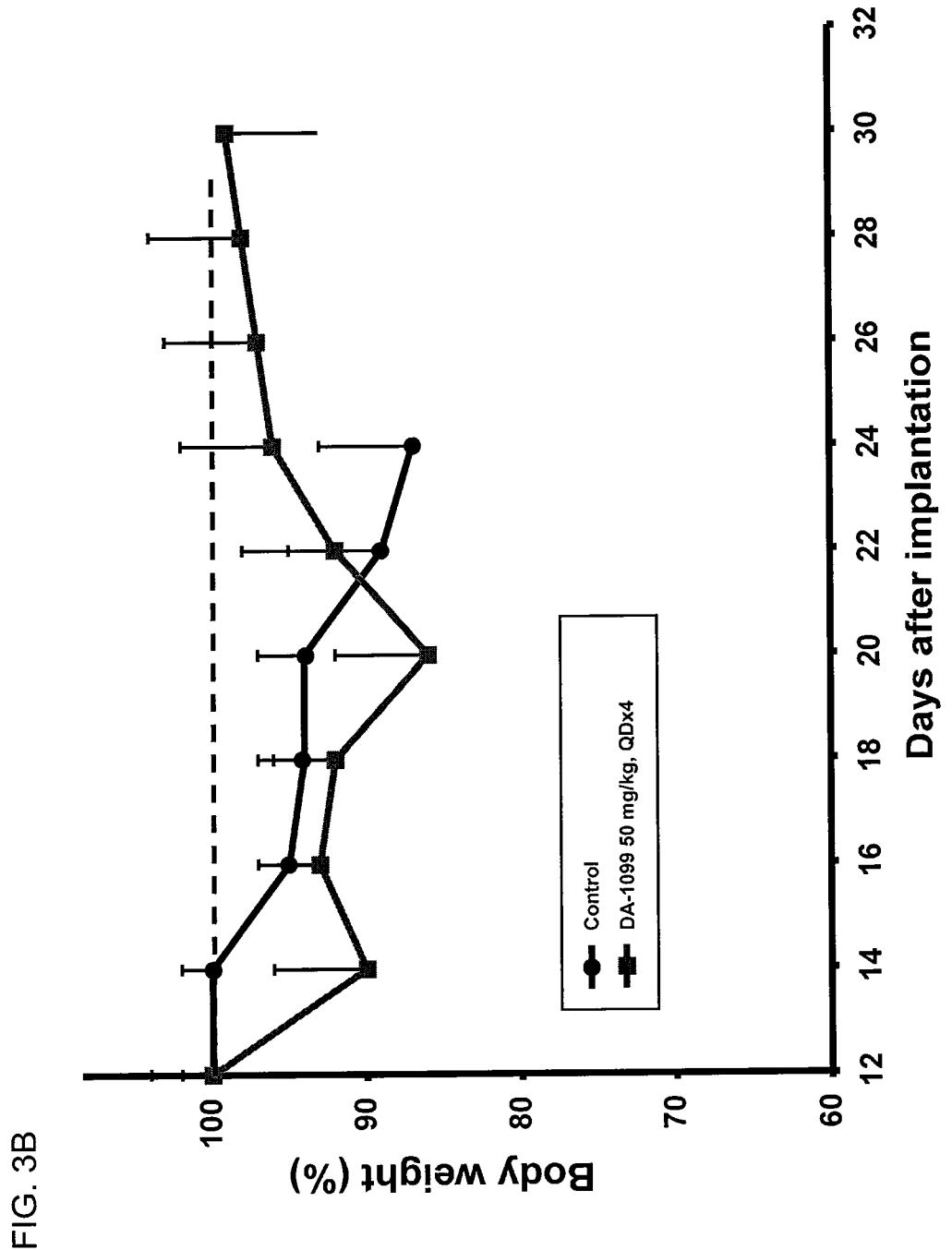
Figure 4A:
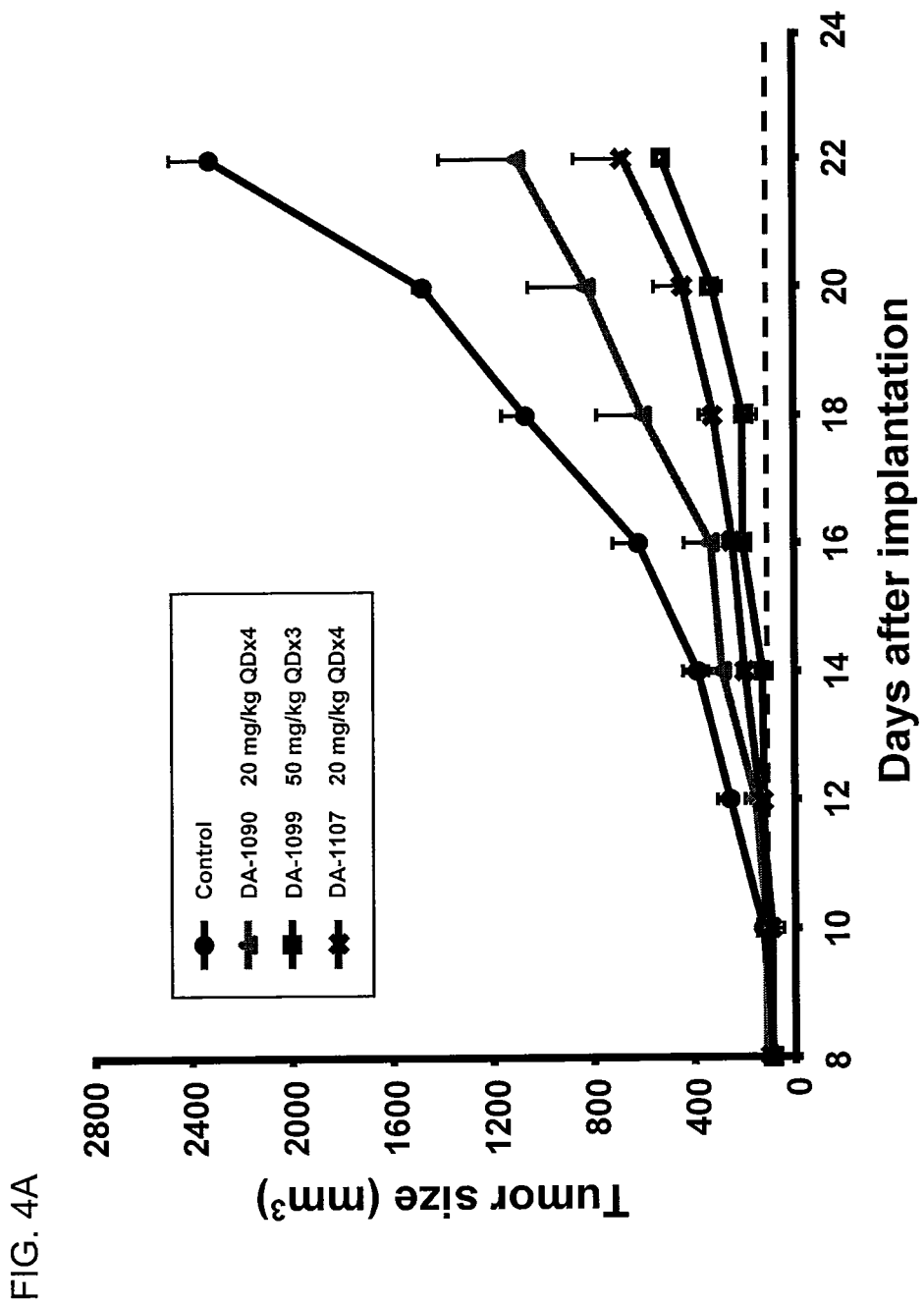
FIGS. 4A-B illustrates the therapeutic effects of DA-1090, 1099, 1107 in nude mice bearing ovarian adenocarcinoma SK-OV-3 xenograft (i.v. inj., n=3), average tumor size changes (FIG. 4A) and average body weight changes (FIG. 4B).
Figure 4B:
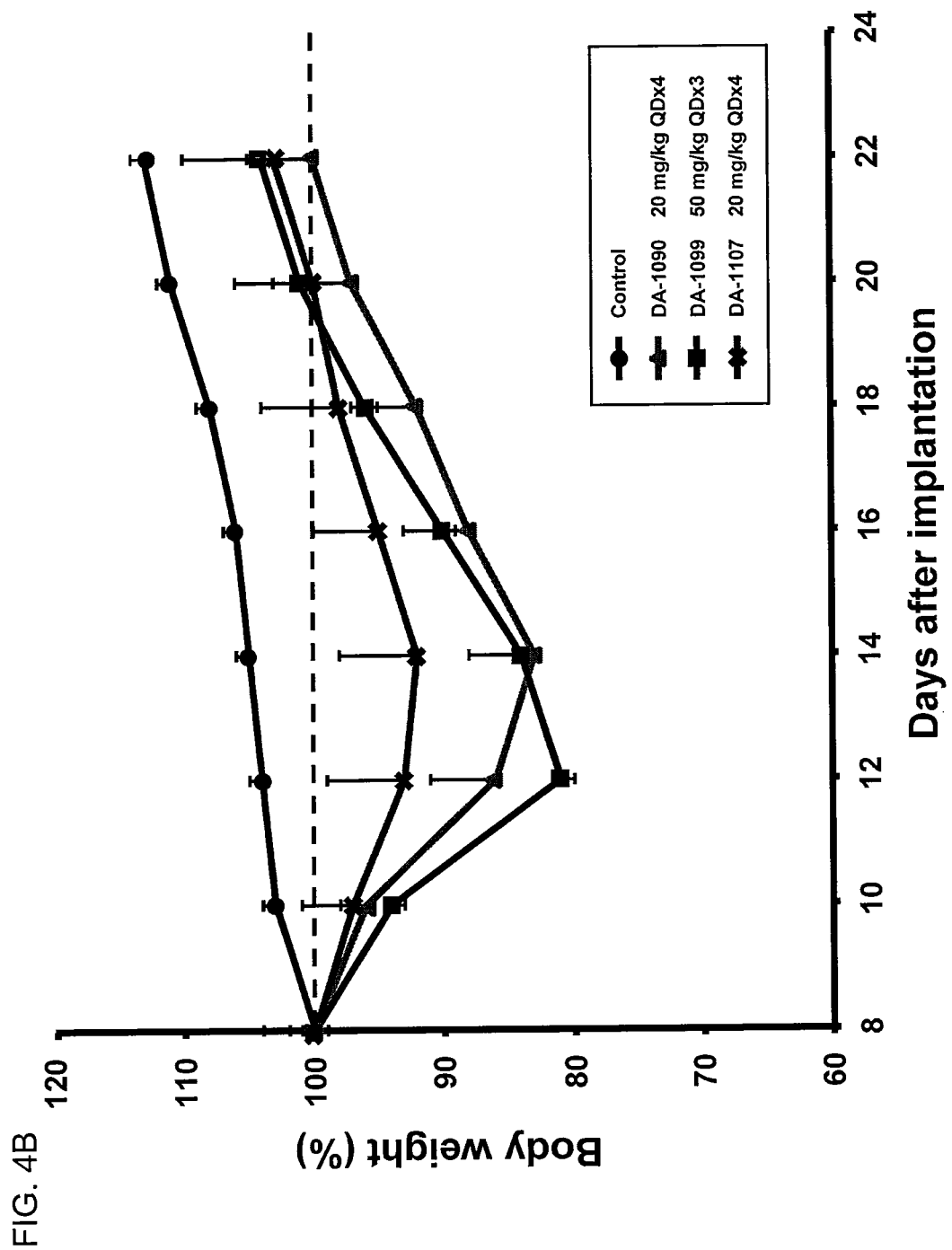

The therapeutic effects of N-mustard DA-1099 against human prostate adenocarcinoma PC-3 s.c. xenograft in nude mice is shown in FIGS. 3, 3A and 3B. xenograft (i.v. inj., n=3), average tumor size changes (FIG. 3A) and average body weight changes (FIG. 3B). As shown in FIG. 3, DA-1099 (50 mg/kg), QD×4, (i.v. inj., n=3), resulted in complete tumor-growth suppression. FIG. 4 shows therapeutic effects of DA-1090, 1099, and 1107 in nude mice bearing ovarian adenocarcinoma SK-OV-3 xenograft (i.v. inj., n=3). Under optimal therapeutic conditions, intravenous injection, of DA-1090, 1099, and 1107, 20 (QD×4), 50 (QD×3), and 20 (QD×4) mg/kg, respectively, yielded 53%, 78%, and 71% tumor suppression, respectively, on day 22.

What is claimed is:

1. A compound of formula I, II, III, or IV:

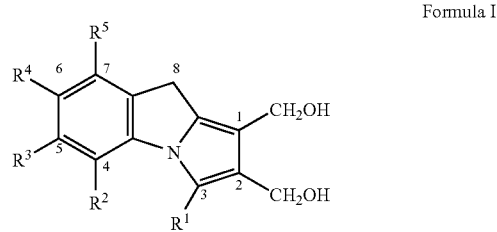

Formula I

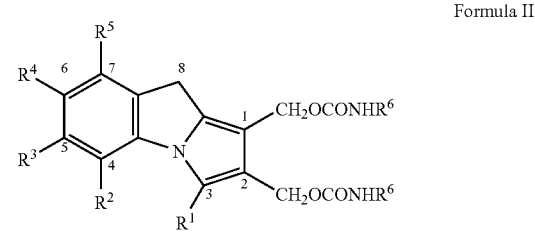

Formula II

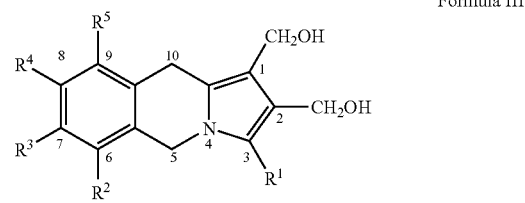

Formula III

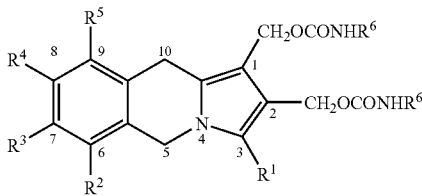

Formula IV and pharmaceutically acceptable salts and mixtures thereof,
wherein:
R¹ is chosen from hydrogen, a $C_1$-$C_5$ linear or branched alkyl group, an aryl, and a benzyl, which may be unsubstituted or substituted;
$R^2$, $R^3$, $R^4$ and $R^5$ are independently chosen from hydrogen, $C_1$-$C_6$ alkyl, $OR^a$, halo, cyano, nitro, $NH_2$, $NHR^b$, and $N(R^b)_2$, wherein $R^a$ is chosen from hydrogen and $C_1$-$C_{10}$ alkyl, and $R^b$ is chosen from hydrogen and $C_1$-$C_{10}$ alkyl; and
$R^6$ is chosen from a saturated or unsaturated, linear or branched, $C_1$-$C_5$ alkyl group, an unsubstituted or substituted phenyl group, and an unsubstitued or substituted benzyl group,
and further wherein: when the $C_1$-$C_5$ linear or branched alkyl group is substituted, one or more substituents are independently chosen from halogen, hydroxy, alkoxy, lower alkyl, lower alkenyl, and lower alkynyl; and
when the aryl, the benzyl, or the phenyl group is substituted, one or more substituents are independently chosen from $C_1$-$C_6$ alkyl, $OR^a$, halo, cyano, nitro, $NH_2$, wherein $R^a$ is as defined above.

2. The compound of formula I according to claim 1, wherein $R^2=R^3=R^5=H$.

3. The compound of formula II according to claim 1, wherein $R^2=R^3=R^5=H$.

4. The compound of formula III according to claim 1, wherein $R^2=R^3=R^4=R^5=H$.

5. The compound of formula IV according to claim 1, wherein $R^2=R^3=R^4=R^5=H$.

6. The compound according to claim 1, wherein the compound is chosen from:
(2-Hydroxymethyl-3-methyl-8H-3a-aza-cyclopenta[a]inden-1-yl)methanol;
(3-Ethyl-2-hydroxymethyl-8H-3a-aza-cyclopenta[a]inden-1-yl)methanol;
(2-Hydroxymethyl-3-propyl-8H-3a-aza-cyclopenta[a]inden-1-yl)methanol;
(2-Hydroxymethyl-3-isopropyl-8H-3a-aza-cyclopenta[a]inden-1-yl)methanol;
(2-Hydroxymethyl-3-butyl-8H-3a-aza-cyclopenta[a]inden-1-yl)methanol;
(2-Hydroxymethyl-3-phenyl-8H-3a-aza-cyclopenta[a]inden-1-yl)methanol;
(2-Hydroxymethyl-3-(2-methoxyphenyl)-8H-3a-aza-cyclopenta[a]inden-1-yl)methanol;
(2-Hydroxymethyl-(4-methoxyphenyl)-8H-3a-aza-cyclopenta[a]inden-1-yl)methanol;
(3-(3,4-Dimethoxyphenyl)-2-hydroxymethyl-8H-3a-aza-cyclopenta[a]inden-1-yl)methanol;
(3-(2,6-Dimethoxyphenyl)-2-hydroxymethyl-8H-3a-aza-cyclopenta[a]inden-1-yl)methanol;
(2-Hydroxymethyl-3-(3,4,5-trimethoxyphenyl)-8H-3-aza-cyclopenta[a]inden-1-yl)-methanol;
(2-Hydroxymethyl-3-(4-methylphenyl)-8H-3a-aza-cyclopenta[a]inden-1-yl)methanol;
(2-Hydroxymethyl-3-(4-nitrophenyl)-8H-3a-aza-cyclopenta[a]inden-1-yl)methanol;
(3-(4-Aminophenyl)-2-hydroxymethyl-8H-3a-aza-cyclopenta[a]inden-1-yl)methanol;
(3-(4-Flourophenyl)-2-hydroxymethyl-8H-3a-aza-cyclopenta[a]inden-1-yl)methanol;
(3-(4-Chlorophenyl)-2-hydroxymethyl-8H-3a-aza-cyclopenta[a]inden-1-yl)methanol;
(3-(3,4-Diflourophenyl)-2-hydroxymethyl-8H-3a-aza-cyclopenta[a]inden-yl)methanol;
(3-(3,4-Dichlorophenyl)-2-hydroxymethyl-8H-3a-aza-cyclopenta[a]inden-1-yl)methanol;
(2-Hydroxymethyl-6-methoxy-3-(4-methoxyphenyl)-8H-3a-aza-cyclopenta[a]inden-1-yl)methanol,
(2-Hydroxymethyl-6-nitro-3-(4-methoxyphenyl)-8H-3a-aza-cyclopenta[a]inden-1-yl)-methanol;
(6-Amino-2-hydroxymethyl-3-(4-methoxyphenyl)-8H-3a-aza-cyclopenta[a]inden-1-yl)methanol;
(2-Hydroxymethyl-6-methyl-3-(4-methoxyphenyl)-8H-3a-aza-cyclopenta[a]inden-1-yl)-methanol;
(6-Chloro-2-hydroxymethyl-3-methyl-8H-3a-aza-cyclopenta[a]inden-1-yl)methanol;
(6-Flouro-2-hydroxymethyl-3-methyl-8H-3a-aza-cyclopenta[a]inden-1-yl)methanol;
(5,6-dimethoxy-2-hydroxymethyl-3-(2-methoxyphenyl)-8H-3a-aza-cyclopenta[a]inden-1-yl)methanol;
(2-hydroxymethyl-4,5,6-trimethoxy-3-methyl-8H-3a-aza-cyclopenta[a]inden-1-yl)methanol;
(6-dimethylamino-2-hydroxymethyl-3-methyl-8H-3a-aza-cyclopenta[a]inden-1-yl)methanol;
Methylcarbamic acid 3-methyl-2-methylcarbamoyloxymethyl-8H-3a-aza-cyclopenta-[a]inden-1-ylmethyl ester;
Methylcarbamic acid 3-ethyl-2-methylcarbamoyloxymethyl-8H-3a-aza-cyclopenta-[a]inden-1-ylmethyl ester;
Methylcarbamic acid 3-propyl-2-methylcarbamoyloxymethyl-8H-3a-aza-cyclopenta[a]inden-1-ylmethyl ester;
Methylcarbamic acid 3-butyl-2-methylcarbamoyloxymethyl-8H-3a-aza-cyclopenta[a]inden-1-ylmethyl ester;
Methylcarbamic acid 3-isopropyl-2-methylcarbamoyloxymethyl-8H-3a-aza-cyclopenta[a]inden-1-yl-methyl ester;
Methylcarbamic acid 2-methylcarbamoyloxymethyl-3-phenyl-8H-3a-aza-cyclopenta[a]inden-1-ylmethyl-ester;
Methylcarbamic acid 3-(4-flourophenyl)-2-methylcarbamoyloxymethyl-8H-3a-aza-cyclopenta[a]inden-1-ylmethyl ester;
Methylcarbamic acid 3-(4-chlorophenyl)-2-methyl-carbamoyloxymethyl-8H-3a-aza-cyclopenta[a]inden-1-ylmethyl ester;
Methylcarbamic acid 3-(3,4-difluorophenyl)-2-methylcarbamoyloxymethyl-8H-3a-aza-cyclopenta[a]inden-1-ylmethyl ester;
Methylcarbamic acid 3-(4-methoxyphenyl)-2-methylcarbamoyloxymethyl-8H-3a-azacyclopenta[a]inden-1-ylmethyl ester;
Methylcarbamic acid 3-(2-methoxyphenyl)-2-methylcarbamoyloxymethyl-8H-3a-aza-cyclopenta[a]inden-1-ylmethyl ester;
Methylcarbamic acid 3-(3,4-dimethoxyphenyl)-2-methylcarbamoyloxymethyl-8H-3a-aza-cyclopenta[a]inden-1-ylmethyl ester;
Methylcarbamic acid 3-(2,6-dimethoxyphenyl)-2-methylcarbamoyloxymethyl-8H-3a-aza-cyclopenta[a]inden-1-ylmethyl ester;
Methylcarbamic acid 3-(3,4,5-trimethoxyphenyl)-2-methylcarbamoyloxymethyl-8H-3a-aza-cyclopenta[a]inden-1-ylmethyl ester;
Methylcarbamic acid 6-methoxy-3-(4-methoxyphenyl)-2-methylcarbamoyloxy-methyl-8H-3a-aza-cyclopenta[a]inden-1-ylmethyl ester;

Methylcarbamic acid 3-(4-methoxyphenyl)-2-methylcarbamoyloxymethyl-6-pyrrolidin-1-yl-8H-3a-aza-cyclopenta[a]inden-1-ylmethyl ester;
Methylcarbamic acid 3-(4-methoxyphenyl)-2-methylcarbamoyloxymethyl-6-piperidin-1-yl-8H-3a-aza-cyclopenta[a]inden-1-ylmethyl ester;
Methylcarbamic acid 3-(4-nitrophenyl)-2-methylcarbamoyloxymethyl-8H-3a-aza-cyclopenta[a]inden-1-ylmethyl ester;
Methylcarbamic acid 3-(4-aminophenyl)-2-methylcarbamoyloxymethyl-8H-3a-aza-cyclopenta[a]inden-1-ylmethyl ester;
Methylcarbamic acid 5,6-methylenedioxy-2-methylcarbamoyloxymethyl-3-(2-methoxyphenyl)-8H-3a-aza-cyclopenta[a]inden-1-ylmethyl ester;
Methylcarbamic acid 5,6-ethylenedioxy-2-methylcarbamoyloxymethyl-3-(2-methoxyphenyl)-8H-3a-aza-cyclopenta[a]inden-1-ylmethyl ester;
Ethylcarbamic acid 2-ethylcarbamoyloxymethyl-3-(4-methoxy-phenyl)-8H-3a-aza-cyclopenta[a]inden-1-ylmethyl ester:
Propylcarbamic acid 3-methyl-2-propylcarbamoyloxymethyl-8H-3a-aza-cyclopenta[a]inden-1-ylmethyl ester;
Isopropylcarbamic acid 2-isopropylcarbamoyloxymethyl-3-methyl-8H-3a-aza-cyclopenta[a]inden-2-ylmethyl ester;
Isobutylcarbamic acid 2-isobutylcarbamoyloxymethyl-3-methyl-8H-3a-aza-cyclopenta[a]inden-2-ylmethyl ester;
Phenylcarbamic acid 3-methyl-2-phenylcarbamoyloxymethyl-8H-3a-aza-cyclopenta[a]inden-1-ylmethyl ester;
(1-Hydroxymethyl-3-methyl-5,10-dihydro-pyrrolo[1,2-b]isoquinolin-2-yl)methanol;
(3-Ethyl-1-hydroxymethyl-5,10-dihydro-pyrrolo[1,2-b]isoquinolin-2-yl)methanol;
(1-Hydroxymethyl-3-phenyl-5,10-dihydro-pyrrolo[1,2-b]isoquinolin-2-yl)methanol;
(3-(4-chlorophenyl)-1-hydroxymethyl-5,10-dihydro-pyrrolo[1,2-b]isoquinolin-2-yl)-methanol;
[3-(4-fluorophenyl)-1-hydroxymethyl-5,10-dihydro-pyrrolo[1,2-b]isoquinolin-2-yl]-methanol;
[3-(3,4-difluorophenyl)-1-hydroxymethyl-5,10-dihydropyrrolo[1,2-b]isoquinolin-2-yl]-methanol;
(1-Hydroxymethyl-3-(2-methoxyphenyl)-5,10-dihydropyrrolo[1,2-b]isoquinolin-2-yl)methanol;
(1-Hydroxymethyl-3-(4-methoxyphenyl)-5,10-dihydropyrrolo[1,2-b]isoquinolin-2-yl)methanol;
[3-(3,4-dimethoxyphenyl)-1-hydroxymethyl-5,10-dihydro-pyrrolo[1,2-b]isoquinolin-2-yl]methanol;
Methylcarbamic acid 3-methyl-2-methylcarbamoyloxymethyl-5,10-dihydropyrrolo-[1,2-b]isoquinolin-1-ylmethyl ester;
Methylcarbamic acid 3-ethyl-2-methylcarbamoyloxymethyl-5,10-dihydropyrrolo-[1,2-b]isoquinolin-1-ylmethyl ester;
Methylcarbamic acid 2-methylcarbamoyloxymethyl-3-phenyl-5,10-dihydropyrrolo-[1,2-b]isoquinolin-1-ylmethyl ester;
Methyl-carbamic acid 3-(4-chlorophenyl)-2-methylcarbamoyloxymethyl-5,10-dihydropyrrolo[1,2-b]isoquinolin-1-ylmethyl ester;
Methylcarbamic acid 3-(4-fluorophenyl)-2-methylcarbamoyloxymethyl-5,10-dihydropyrrolo[1,2-b]isoquinolin-1-ylmethyl ester;
Methylcarbamic acid 3-(3,4-diflourophenyl)-2-methylcarbamoyloxymethyl-5,10-dihydropyrrolo[1,2-b]isoquinolin-1-ylmethyl ester;
Methylcarbamic acid 3-(2-methoxyphenyl)-2-methylcarbamoyloxymethyl-5,10-dihydropyrrolo[1,2-b]isoquinolin-1-ylmethyl ester;
Methylcarbamic acid 3-(4-methoxyphenyl)-2-methylcarbamoyloxymethyl-5,10-dihydropyrrolo[1,2-b]isoquinolin-1-ylmethyl ester;
Methylcarbamic acid 3-(3,4-dimethoxyphenyl)-2-methylcarbamoyloxymethyl-5,10-dihydropyrrolo[1,2-b]isoquinolin-1-ylmethyl ester;
Propylcarbamic acid 3-methyl-2-propylcarbamoyloxymethyl-5,10-dihydropyrrolo-[1,2-b]isoquinolin-1-ylmethyl ester;
Propylcarbamic acid 3-ethyl-2-propylcarbamoyloxymethyl-5,10-dihydropyrrolo-[1,2-b]isoquinolin-1-ylmethyl ester;
Propylcarbamic acid 3-phenyl-2-propylcarbamoylmethyl-5,10-dihydropyrrolo-[1,2-b]isoquinolin-1-ylmethyl ester;
Propylethylcarbamic acid 3-(4-chlorophenyl)-2-propylcarbamoyloxymethyl-5,10-dihydropyrrolo[1,2-b]isoquinolin-1-ylmethyl ester;
Propylcarbamic acid 3-(4-fluorophenyl)-2-propylcarbamoyloxymethyl-5,10-dihydropyrrolo[1,2-b]isoquinolin-1-ylmethyl ester;
Propylcarbamic acid 3-(3,4-diflourophenyl)-2-propylcarbamoyloxymethyl-5,10-dihydropyrrolo[1,2-b]isoquinolin-1-ylmethyl ester;
Propylcarbamic acid 3-(4-methoxyphenyl)-2-propylcarbamoyloxymethyl-5,10-dihydropyrrolo[1,2-b]isoquinolin-1-ylmethyl ester; and
Propylcarbamic acid 3-(3,4-dimethoxyphenyl)-2-propylcarbamoyloxymethyl-5,10-dihydropyrrolo[1,2-b]isoquinolin-1-ylmethyl ester.

7. The compound according to claim 1, wherein the compound is chosen from:
(2-Hydroxymethyl-3-methyl-8H-3a-aza-cyclopenta[a]inden-1-yl)methanol;
(3-Ethyl-2-hydroxymethyl-8H-3a-aza-cyclopenta[a]inden-1-yl)methanol;
(2-Hydroxymethyl-3-phenyl-8H-3a-aza-cyclopenta[a]inden-1-yl)methanol;
(2-Hydroxymethyl-3-(2-methoxyphenyl)-8H-3a-aza-cyclopenta[a]inden-1-yl)methanol;
(2-Hydroxymethyl-3-(4-methoxyphenyl)-8H-3a-aza-cyclopenta[a]inden-1-yl)methanol;
(3-(3,4-Dimethoxyphenyl)-2-hydroxymethyl-8H-3a-aza-cyclopenta[a]inden-1-yl)methanol;
(3-(2,6-Dimethoxyphenyl)-2-hydroxymethyl-8H-3a-aza-cyclopenta[a]inden-1-yl)methanol;
(2-Hydroxymethyl-3-(3,4,5-trimethoxyphenyl)-8H-3a-aza-cyclopenta[a]inden-1-yl)-methanol;
(3-(4-Fluorophenyl)-2-hydroxymethyl-8H-3a-aza-cyclopenta[a]inden-1-yl)methanol;
(3-(4-Chlorophenyl)-2-hydroxymethyl-8H-3a-aza-cyclopenta[a]inden-1-yl)methanol;
(3-(3,4-Difluorophenyl)-2-hydroxymethyl-8H-3a-aza-cyclopenta[a]inden-1-yl)methanol;
(2-Hydroxymethyl-6-methoxy-3-(4-methoxyphenyl)-8H-3a-aza-cyclopenta[a]inden-1-yl)methanol;
Methylcarbamic acid 3-methyl-2-methylcarbamoyloxymethyl-8H-3a-aza-cyclopenta-[a]inden-1-ylmethyl ester;
Methylcarbamic acid 3-ethyl-2-methylcarbamoyloxymethyl-8H-3a-aza-cyclopenta-[a]inden-1-ylmethyl ester;
Methyl-carbamic acid 2-methylcarbamoyloxymethyl-3-phenyl-8H-3a-aza-cyclo-penta[a]inden-1-ylmethyl ester;
Methylcarbamic acid 3-(4-fluorophenyl)-2-methylcarbamoyloxymethyl-8H-3a-aza-cyclopenta[a]inden-1-ylmethyl ester;

Methylcarbamic acid 3-(4-chlorophenyl)-2-methyl-carbamoyloxymethyl-8H-3a-aza-cyclopenta[a]inden-1-ylmethyl ester;

Methylcarbamic acid 3-(3,4-difluorophenyl)-2-methylcarbamoyloxymethyl-8H-3a-aza-cyclopenta[a]inden-1-ylmethyl ester;

Methylcarbamic acid 3-(4-methoxy-phenyl)-2-methylcarbamoyloxymethyl-8H-3a-azacyclopenta[a]inden-1-ylmethyl ester;

Methylcarbamic acid 3-(2-methoxyphenyl)-2-methylcarbamoyloxymethyl-8H-3a-aza-cyclopenta[a]inden-1-ylmethyl ester;

Methylcarbamic acid 3-(3,4-dimethoxyphenyl)-2-methyl-carbamoyloxymethyl-8H-3a-aza-cyclopenta[a]inden-1-ylmethyl ester;

Methylcarbamic acid 3-(2,6-dimethoxyphenyl)-2-methyl-carbamoyloxymethyl-8H-3a-aza-cyclopenta[a]inden-1-ylmethyl ester;

Methylcarbamic acid 3-(3,4,5-trimethoxyphenyl)-2-methylcarbamoyloxymethyl-8H-3a-aza-cyclopenta[a]inden-1-ylmethyl ester;

Methylcarbamic acid 6-methoxy-3-(4-methoxyphenyl)-2-methylcarbamoyloxy-methyl-8H-3a-aza-cyclopenta[a]inden-1-ylmethyl ester;

(1-Hydroxymethyl-3-methyl-5,10-dihydro-pyrrolo[1,2-b]isoquinolin-2-yl)methanol;

(3-(4-chlorophenyl)-1-hydroxymethyl-5,10-dihydro-pyrrolo[1,2-b]isoquinolin-2-yl)-methanol;

[3-(3,4-difluorophenyl)-1-hydroxymethyl-5,10-dihydro-pyrrolo[1,2-b]isoquinolin-2-yl]-methanol;

(1-Hydroxymethyl-3-(4-methoxyphenyl)-5,10-dihydro-pyrrolo[1,2-b]isoquinolin-2-yl)methanol;

Methylcarbamic acid 3-methyl-2-methylcarbamoyloxymethyl-5,10-dihydropyrrolo-[1,2-b]isoquinolin-1-ylmethyl ester;

Methyl-carbamic acid 3-(4-chlorophenyl)-2-methylcarbamoyloxymethyl-5,10-dihydropyrrolo[1,2-b]isoquinolin-1-ylmethyl ester;

Methylcarbamic acid 3-(3,4-difluorophenyl)-2-methylcarbamoyloxymethyl-5,10-dihydropyrrolo[1,2-b]isoquinolin-1-ylmethyl ester;

and

Methylcarbamic acid 3-(4-methoxyphenyl)-2-methylcarbamoyloxymethyl-5,10-dihydropyrrolo[1,2-b]isoquinolin-1-ylmethyl ester.

8. A pharmaceutical composition comprising the compound of claim 1 and at least one pharmaceutically acceptable excipient.

9. The compound according to claim 1, wherein the compound is chosen from:
(2-Hydroxymethyl-3-methyl-8H-3a-aza-cyclopenta[a]inden-1-yl)methanol; and
(3-Ethyl-2-hydroxymethyl-8H-3a-aza-cyclopenta[a]inden-1-yl)methanol.

10. The compound according to claim 1 wherein the compound is:
Methylcarbamic acid 3-(4-methoxyphenyl)-2-methylcarbamoyloxymethyl-8H-3a-azacyclopenta[a]inden-1-ylmethyl ester;
Methylcarbamic acid 3-(2-methoxyphenyl)-2-methylcarbamoyloxymethyl-8H-3a-aza-cyclopenta[a]inden-1-ylmethyl ester; and
Ethylcarbamic acid 2-ethylcarbamoyloxymethyl-3-(4-methoxy-phenyl)-8H-3a-aza-cyclopenta[a]inden-1-ylmethyl ester.

11. The compound according to claim 1, wherein the compound is (1-Hydroxymethyl-3-methyl-5,10-dihydro-pyrrolo[1,2-b]isoquinolin-2-yl)methanol.

12. The pharmaceutical composition according to claim 8, wherein the compound is chosen from the compounds of claims 9, 10, and 11.

13. The compound according to claim 1, wherein $R^2$, $R^3$, $R^4$ and $R^5$ are independently chosen from hydrogen and methoxy.

14. A method of inhibiting cancer cell growth, comprising administering an effective amount of the compound of claim 13 to a mammal in need thereof, wherein the cancer is chosen from lung cancer, bladder cancer, colon cancer, prostate cancer, breast cancer, ovarian cancer, oral cancer, leukemia, brain cancer, vinblastine-resistant cancer, and taxol-resistant cancer.

15. A method of killing cancer cells comprising providing an effective amount of the compound of claim 13 to cancer cells, wherein the cancer is chosen from lung cancer, bladder cancer, colon cancer, prostate cancer, breast cancer, ovarian cancer, oral cancer, leukemia, brain cancer, vinblastine-resistant cancer, and taxol-resistant cancer.

16. A method of treating cancer, comprising administering an effective amount of the compound of claim 13 to a mammal in need thereof, wherein the cancer is chosen from lung cancer, bladder cancer, colon cancer, prostate cancer, breast cancer, ovarian cancer, oral cancer, leukemia, brain cancer, vinblastine-resistant cancer, and taxol-resistant cancer.

17. The method according to claim 16, wherein the compound is chosen from the compounds of claim 6.

18. The method according to claim 16, wherein the compound is chosen from the compounds of claim 7.

19. The method of claim 16 wherein the compound is administered in combination with another form of therapy.

20. The method of dam 16, wherein the compound is administered in conjunction with radiation therapy, immunotherapy, monoclonal antibody therapy, hormonal therapy, chemotherapy using other agents, and/or surgery.

21. The method of treating cancer according to claim 16, wherein the compound is chosen from the compounds of claims 9, 10, and 11.

* * * * *

UNITED STATES PATENT AND TRADEMARK OFFICE
CERTIFICATE OF CORRECTION

PATENT NO. : 8,410,130 B2
APPLICATION NO. : 12/267227
DATED : April 2, 2013
INVENTOR(S) : Tsann-Long Su et al.

It is certified that error appears in the above-identified patent and that said Letters Patent is hereby corrected as shown below:

In the Claims:

Claim 6, col. 41, lines 56-57, "(2-Hydroxymethyl-(4-methoxyphenyl)-8H-3a-aza-cyclopenta[a]inden-1-yl)methanol;" should read --(2-Hydroxymethyl-3-(4-methoxyphenyl)-8H-3a-aza-cyclopenta[a]inden-1-yl)methanol;--.

Claim 6, col. 41, lines 62-63, "(2-Hydroxymethyl-3-(3,4,5-trimethoxyphenyl)-8H-3-aza-cyclopenta[a]inden-1-yl)-methanol;" should read -- (2-Hydroxymethyl-3-(3,4,5-trimethoxyphenyl)-8H-3a-aza-cyclopenta[a]inden-1-yl)-methanol;--.

Claim 6, col. 42, lines 3-4, "(3-(4-Flourophenyl)-2-hydroxymethyl-8H-3a-aza-cyclopenta[a]inden-1-yl)methanol;" should read -- (3-(4-Fluorophenyl)-2-hydroxymethyl-8H-3a-aza-cyclopenta[a]inden-1-yl)methanol;--.

Claim 6, col. 42, lines 7-8, "(3-(3,4-Diflourophenyl)-2-hydroxymethyl-8H-3a-aza-cyclopenta[a]inde- n-yl)methanol;" should read -- (3-(3,4-Difluorophenyl)-2-hydroxymethyl-8H-3a-aza-cyclopenta[a]inde- n-yl)methanol;--.

Claim 6, col. 42, lines 21-22, "(6-Flouro-2-hydroxymethyl-3-methyl-8H-3a-aza-cyclopenta[a]inden-1-yl)methanol;" should read -- (6-Fluoro-2-hydroxymethyl-3-methyl-8H-3a-aza-cyclopenta[a]inden-1-yl)methanol;--.

Claim 6, col. 42, lines 42-44, "Methylcarbamic acid 3-(4-flourophenyl)-2-methylcarbamoyloxymethyl-8H-3a-aza- cyclopenta[a]inden-1-ylmethyl ester;" should read -- Methylcarbamic acid 3-(4-fluorophenyl)-2-methylcarbamoyloxymethyl-8H-3a-aza- cyclopenta[a]inden-1-ylmethyl ester;--.

Claim 6, col. 43, lines 65-67, "Methylcarbamic acid 3-(3,4-diflourophenyl)-2-methylcarbamoyloxymethyl-5,10- dihydropyrrolo[1,2-b]isoquinolin-1-ylmethyl ester;"

Signed and Sealed this
Twenty-fourth Day of September, 2013

Teresa Stanek Rea
*Deputy Director of the United States Patent and Trademark Office* should read -- Methylcarbamic acid 3-(3,4-difluorophenyl)-2-methylcarbamoyloxymethyl-5,10- dihydropyrrolo[1,2-b]isoquinolin-1-ylmethyl ester;--.

Claim 20, col. 46, line 47, "The method of dam 16," should read -- The method of claim 16,--.